US012329833B2

(12) United States Patent
Abuelyaman et al.

(10) Patent No.: US 12,329,833 B2
(45) Date of Patent: Jun. 17, 2025

(54) DENTAL COMPOSITIONS

(71) Applicant: Solventum Intellectual Properties Company, Maplewood, MN (US)

(72) Inventors: Ahmed S. Abuelyaman, Woodbury, MN (US); Amanda K. Leone, St. Paul, MN (US); Guy D. Joly, Shoreview, MN (US); Joel D. Oxman, Minneapolis, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 0 days.

(21) Appl. No.: 18/712,829

(22) PCT Filed: Nov. 1, 2022

(86) PCT No.: PCT/IB2022/060513
§ 371 (c)(1),
(2) Date: May 23, 2024

(87) PCT Pub. No.: WO2023/105315
PCT Pub. Date: Jun. 15, 2023

(65) Prior Publication Data
US 2025/0049644 A1    Feb. 13, 2025

Related U.S. Application Data

(60) Provisional application No. 63/265,005, filed on Dec. 6, 2021.

(51) Int. Cl.
*A61K 6/887* (2020.01)

(52) U.S. Cl.
CPC .................................. *A61K 6/887* (2020.01)

(58) Field of Classification Search
None
See application file for complete search history.

(56) References Cited

U.S. PATENT DOCUMENTS

| | | | |
|---|---|---|---|
| 4,503,169 A | 3/1985 | Randklev | |
| 4,547,323 A | 10/1985 | Carlson | |
| 4,886,861 A | 12/1989 | Janowicz | |
| 5,324,879 A | 6/1994 | Hawthorne | |
| 6,284,898 B1 | 9/2001 | Moszner | |
| 6,387,981 B1 | 5/2002 | Zhang et al. | |
| 6,572,693 B1 | 6/2003 | Wu et al. | |
| 6,730,156 B1 | 5/2004 | Windisch et al. | |
| 6,794,520 B1 | 9/2004 | Moszner | |
| 7,090,721 B2 | 8/2006 | Craig et al. | |
| 7,090,722 B2 | 8/2006 | Budd et al. | |
| 7,156,911 B2 | 1/2007 | Kangas | |
| 7,241,437 B2 | 7/2007 | Davidson | |
| 7,649,029 B2 | 1/2010 | Kolb et al. | |
| 7,674,850 B2 | 3/2010 | Karim et al. | |
| 8,647,510 B2 | 2/2014 | Kolb et al. | |
| 9,056,043 B2 * | 6/2015 | Joly | A61K 6/30 |
| 9,403,966 B2 | 8/2016 | Joly | |
| 9,907,733 B2 | 3/2018 | Joly et al. | |
| 2006/0009574 A1 * | 1/2006 | Aert | C09D 11/107 |
| | | | 524/832 |
| 2008/0194722 A1 | 8/2008 | Abuelyaman | |
| 2015/0238389 A1 * | 8/2015 | Moser | A61K 6/61 |
| | | | 523/118 |
| 2017/0210693 A1 | 7/2017 | Joly | |
| 2023/0323151 A1 * | 10/2023 | Joly | C09D 7/68 |
| | | | 524/548 |

FOREIGN PATENT DOCUMENTS

| | | |
|---|---|---|
| JP | H07196867 A | 8/1995 |
| JP | 2014513154 A | 5/2014 |
| WO | 0130305 W | 5/2001 |
| WO | 200130307 A1 | 5/2001 |
| WO | 2003063804 A1 | 8/2003 |
| WO | 2008082881 A1 | 7/2008 |
| WO | 2011126647 A2 | 10/2011 |
| WO | 2012003136 A1 | 1/2012 |
| WO | 2012112304 A1 | 8/2012 |
| WO | 2023105327 A1 | 6/2023 |

OTHER PUBLICATIONS

U.S. Appl. No. 18/712,829 STIC structure search (Year: 2024).*
Cara, R. R., Nicola, et al. "Influence of Bis-GMA Derivative Monomer-Based Particulate Composite Resins on the Cuspal Deformation and Microleakage of Restored Teeth". Particulate Science and Technology, 28(3), (2010). p. 191-206.
Hutson, Lillian et al. "Chain Transfer Activity of ω-Unsaturated Methacrylic Oligomers in Polymerizations of Methacrylic Monomers." Macromolecules 37.12 (2004): 4441-4452.
International Search Report for PCT International Application No. PCT/IB2022/060513, dated Jan. 16, 2023, 4 pages.
Moad, Catherine L et al. "Chain Transfer Activity of ω-Unsaturated Methyl Methacrylate Oligomers." Macromolecules 29.24 (1996): 7717-7726.
Ploehn, Harry J. "Surface and Colloid Science. Edited by Egon Matijevic, vol. 15, Plenum, New York, 1993, 276 pp." AIChE Journal 1995: 743-745.
Sakaguchi, "Testing of Dental Materials and Biomechanics" Craig's Restorative Dental Materials, 13th Edition., (2012), p. 86.
Yuanxian Wang et al., Poly(α-methyleneglutarimide)s from radical polymerization of α-methyleneglutarimides, Journal of Polymer Science, Part A: Polymer Chemistry, 2018, 56, 1020-1026, DOI: 10.1002/pola.28977.

* cited by examiner

*Primary Examiner* — Peter A Salamon

(57) ABSTRACT

A dental composition is provided. The dental composition includes at least one monomer comprising at least two ethylenically unsaturated groups; and an addition-fragmentation agent comprising at least one cyclic imide monomer comprising an α, β-unsaturated carbonyl.

18 Claims, No Drawings

DENTAL COMPOSITIONS

CROSS REFERENCE TO RELATED APPLICATIONS

This application is a national stage filing under 35 U.S.C. 371 of PCT/IB2022/060513, filed Nov. 1, 2022 which claims the benefit of U.S. Provisional Application No. 63/265,005 filed Dec. 6, 2021 the disclosure of which is incorporated by reference in its/their entirety herein.

BACKGROUND

Polymerizable dental compositions that include addition-fragmentation agents have been described in, for example, U.S. Pat. Nos. 9,056,043 and 9,907,733.

DETAILED DESCRIPTION

Polymerization-based stress is caused by the material contracting during curing. This volumetric shrinkage leads to many problems including cracking, reduced durability, decreased lifetime, and residual internal stress. Consequently, reducing polymerization shrinkage and shrinkage stress is of interest in industry.

Various methods for reducing stress have been identified (e.g., cleavable cross-linkers, slowing the cure to delay the material's transition from viscous to elastic, and/or adding monomers that fragment then add to the polymeric network during the polymerization). Certain monomers have been developed that fragment-add during curing, which demonstrate significant performance in reducing shrinkage-stress in free-radically cured dental composites and structural adhesives. However, additional monomers that can contribute to further reductions in the stress of dental composites are desirable.

As used herein, "dental composition" refers to a material, optionally comprising filler, capable of adhering or being bonded to an oral surface. A curable dental composition can be used to bond a dental article to a tooth structure, form a coating (e.g., a sealant or varnish) on a tooth surface, be used as a restorative that is placed directly into the mouth and cured in-situ, or alternatively be used to fabricate a prosthesis outside the mouth that is subsequently adhered within the mouth.

Curable dental compositions include, for example, adhesives (e.g., dental and/or orthodontic adhesives), cements (e.g., resin-modified glass ionomer cements, and/or orthodontic cements), primers (e.g., orthodontic primers), liners (applied to the base of a cavity to reduce tooth sensitivity), coatings such as sealants (e.g., pit and fissure), and varnishes; and resin restoratives (also referred to as direct composites) such as dental fillings, as well as crowns, bridges, and articles for dental implants. Highly filled dental compositions are also used for mill blanks, from which a crown may be milled. Dental cements are somewhat less filled and less viscous materials than composites, and typically act as a bonding agent for additional materials, such as inlays, onlays and the like, or act as the filling material itself if applied and cured in layers. Dental cements are also used for permanently bonding dental restorations such as a crown or bridge to a tooth surface or an implant abutment.

As used herein: "dental article" refers to an article that can be adhered (e.g., bonded) to a tooth structure or dental implant. Dental articles include, for example, crowns, bridges, veneers, inlays, onlays, fillings, orthodontic appliances and devices;

"addition-fragmentation agent" refers to a monomer that includes a fragmentable ethylenically unsaturated group (i.e., a group that fragments during curing by a homolytic bond breakage (including a ring opening)) and that may have within its structure at least one additional free radically polymerizable group (e.g., a (meth)acrylate group);

"orthodontic appliance" refers to any device intended to be bonded to a tooth structure, including, but not limited to, orthodontic brackets, buccal tubes, lingual retainers, orthodontic bands, bite openers, buttons, and cleats. The appliance has a base for receiving adhesive and it can be a flange made of metal, plastic, ceramic, or combinations thereof. Alternatively, the base can be a custom base formed from cured adhesive layer(s) (i.e. single or multi-layer adhesives);

"oral surface" refers to a soft or hard surface in the oral environment. Hard surfaces typically include tooth structure including, for example, natural and artificial tooth surfaces, bone, and the like;

"hardenable" and "curable' is descriptive of a material or composition that can be cured (e.g., polymerized or cross-linked) by heating to induce polymerization and/or cross-linking; irradiating with actinic irradiation to induce polymerization and/or crosslinking; and/or by mixing one or more components to induce polymerization and/or crosslinking. "Mixing" can be performed, for example, by combining two or more parts to form a homogeneous composition. Alternatively, two or more parts can be provided as separate layers that intermix (e.g., spontaneously or upon application of shear stress) at the interface to initiate polymerization;

"hardened" refers to a material or composition that has been at least partially cured (e.g., polymerized or cross-linked);

"hardener" refers to something that initiates hardening of a resin. A hardener may include, for example, a polymerization initiator system, a photoinitiator system, a thermal initiator and/or a redox initiator system;

"(meth)acrylate" is a shorthand reference to acrylate, methacrylate, or combinations thereof; "(meth)acrylic" is a shorthand reference to acrylic, methacrylic, or combinations thereof; and "(meth)acryl" is a shorthand reference to acryl, methacryl, or combinations thereof;

"acryloyl" is used in a generic sense and mean not only derivatives of acrylic acid, but also amine, and alcohol derivatives, respectively;

"(meth)acryloyl" includes both acryloyl and methacryloyl groups; i.e. is inclusive of both esters and amides;

"alkyl" includes straight-chained, branched, and cyclic alkyl groups and includes both unsubstituted and substituted alkyl groups. Unless otherwise indicated, the alkyl groups typically contain from 1 to 20 carbon atoms. Examples of "alkyl" as used herein include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, and norbornyl, and the like. Unless otherwise noted, alkyl groups may be mono- or polyvalent, i.e monovalent alkyl or polyvalent alkylene;

"heteroalkyl" includes both straight-chained, branched, and cyclic alkyl groups with one or more heteroatoms independently selected from S, O, and N with both unsubstituted and substituted alkyl groups. Unless otherwise indicated, the heteroalkyl groups typically contain from 1 to 20 carbon atoms. "Heteroalkyl" is a subset of "hydrocarbyl containing one or more S, N, O, P, or Si atoms" described below. Examples of "heteroalkyl" as used herein include, but are not limited to, methoxy, ethoxy, propoxy, 3,6-dioxaheptyl, 3-(trimethylsilyl)-propyl, 4-dimethylaminobutyl, and the like. Unless otherwise noted, heteroalkyl groups may be mono- or polyvalent, i.e. monovalent heteroalkyl or polyvalent heteroalkylene;

"aryl" is an aromatic group containing 5-18 ring atoms and can contain optional fused rings, which may be saturated, unsaturated, or aromatic. Examples of an aryl groups include phenyl, naphthyl, biphenyl, phenanthryl, and anthracyl. Heteroaryl is aryl containing 1-3 heteroatoms such as nitrogen, oxygen, or sulfur and can contain fused rings. Some examples of heteroaryl groups are pyridyl, furanyl, pyrrolyl, thienyl, thiazolyl, oxazolyl, imidazolyl, indolyl, benzofuranyl, and benzthiazolyl. Unless otherwise noted, aryl and heteroaryl groups may be mono- or polyvalent, i.e. monovalent aryl or polyvalent arylene; and As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

In some embodiments, the present disclosure is directed to polymerizable dental compositions that may include a curable component that includes (i) an addition-fragmentation agent that includes a cyclic imide monomer; (ii) optionally, an addition-fragmentation agent (not including those that include a cyclic imide monomer) that includes a fragmentable ethylenically unsaturated group within its structure that has at least one free radically polymerizable group; and (iii) at least one ethylenically unsaturated monomer or oligomer.

Generally, it has been discovered that dental composites containing the present cyclic imide monomers as stress-reducing additives exhibit greatly reduced polymerization-based stress in free-radically cured dental composites relative to that of known stress-reducing monomers (and without diminishing the mechanical properties of the cured composition). Moreover, it has been discovered that dental composites that include both the present cyclic imide monomers and certain known monomers that fragment during curing (sometimes referred to herein as addition-fragmentation agents) outperform relative to composites that include either the present cyclic imide monomers or the certain addition-fragmentation agents alone.

In some embodiments, the curable component of the present disclosure may include an addition fragmentation agent that includes one or more cyclic imide monomers comprising an α, β-unsaturated carbonyl. In some embodiments, the cyclic imide monomers can act as addition-fragmentation agents in a polymerizable composition (e.g., free-radical polymerizable composition).

In some embodiments, the cyclic imide monomers may include at least one imide group consisting of two acyl groups bound to nitrogen. The cyclic imide monomer described herein may further include an alpha, beta-unsaturation (α,β-unsaturation), i.e. a pi bond between the alpha- and beta-carbons adjacent to a carbonyl group. In some embodiments, the cyclic imide monomer may further include a quaternary carbon atom at the gamma position (referred to herein as a γ-quaternary carbon atom) (i.e., a carbon atom that is three away from the carbon atom of the carbonyl group adjacent the α,β-unsaturation). It is to be appreciated that, in some embodiments, the presence of a quaternary carbon atom at the gamma position is a main driver for the ring-opening step (discussed in more detail below).

The cyclic imide monomers may be prepared by reacting a dicarboxylic acid comprising an α,β-unsaturated carbonyl with a dehydrating agent, such as acetic anhydride, forming a cyclic compound comprising an anhydride group and an α, β-unsaturated carbonyl; and reacting the anhydride group with an (e.g. primary) amine compound.

In some embodiments, the dicarboxylic acids comprise at least three contiguous carbon atoms having an α,β-unsaturated carbonyl between the acid groups. Thus, the imide group and a pendant alpha, beta-unsaturation are typically present in a heterocyclic molecule wherein the ring comprises at least 6 covalently bonded atoms. In other words, the cyclic imide monomers described herein comprise one or more heterocyclic rings wherein the ring(s) comprise 6 or more covalently bonded atoms in a heterocyclic ring, the heterocyclic ring comprising both an imide group and an α β-unsaturated carbonyl.

In some embodiments, representative dicarboxylic acids that include an α,β-unsaturated carbonyl is depicted as follows:

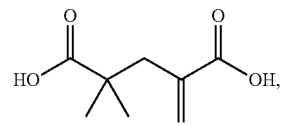

2,2,-dimethyl-4-methylidenepentanedioic acid (also described as 2,4-biscarboxy-4-methylpent-1-ene or 2,2-dimethyl-4-methylene glutaric acid).

In some embodiments, such dicarboxylic acid is used to prepare a cyclic imide monomer comprising a single ring. The cyclic imide monomer may have the structure

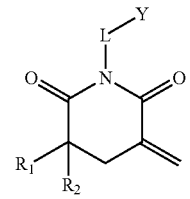

wherein L is a covalent bond or an organic linking group; Y is alkyl, aryl, hydroxyl, carboxylic acid, or a an ethylenically unsaturated group; and $R_1$ and $R_2$ are independently alkyl groups.

In some embodiments, $R_1$ and $R_2$ are independently C1 to C18 alkyl groups, C1 to C16 alkyl groups, C1 to C10 alkyl groups, or C1 to C4 alkyl groups (e.g. methyl, ethyl, propyl, or butyl). In some embodiments, $R_1$ and $R_2$ are alkyl substituents such that the cyclic imide monomer ring-opens during polymerization thereby forming radicals.

L typically comprises (hetero)alkylene, (hetero)arylene, or a combination thereof. In some embodiments, the alkylene or arylene linking group (i.e. L) may comprises heteroatoms, such oxygen. For example, L may comprise one or more ester moieties, one or more urethane moieties, and/or one or more pendent hydroxyl groups.

In some embodiments, 2,2-dimethyl-4-methylene glutaric anhydride is used to prepare a cyclic imide monomer comprising two rings or in other words a cyclic bis-imide. The cyclic bis-imide monomer may have the structure:

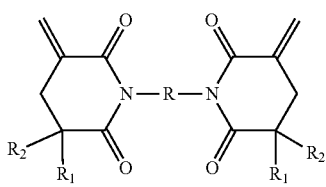

wherein R is an organic linking group, and
  $R_1$ and $R_2$ are independently substituents, as previously described.
  R typically comprises (hetero)alkylene, (hetero)arylene, or a combination thereof.

In some embodiments, the alkylene or arylene linking group (i.e. R) may comprise heteroatoms, such oxygen or nitrogen. For example, R may comprise one or more ester moieties, one or more urethane moieties, and/or one or more pendent hydroxyl groups. R may optionally further comprise a pendent ethylenically unsaturated group In some embodiments, the cyclic imide monomer comprises at least one (e.g. free-radically polymerizable) ethylenically unsaturated group in combination with the α,β-unsaturation. In this embodiment, Y is a (e.g. free-radically polymerizable) ethylenically unsaturated group or R of the cyclic bis-imide further comprises a pendent (e.g. free-radically polymerizable) ethylenically unsaturated group. In this embodiment, the number of ethylenically unsaturated polymerizable groups of the cyclic imide monomer is ≥2. In some embodiments, the number of ethylenically unsaturated polymerizable groups of the cyclic imide monomer is no greater than 3.

The one or more additional ethylenically unsaturated groups may include, but are not limited to the following structures, include for example (meth)acryl (i.e. (meth) acryloyl and (meth)acrylamide), vinyl, styrenic and ethynyl.

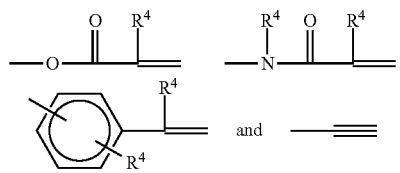

Wherein each $R^4$ is independently H or $C_1$-$C_4$ alkyl.

Some representative cyclic imide monomers are as follows:

TABLE A

| Imide-Based Addition-Fragmentation Monomers | |
| --- | --- |
| Cyclic imide monomers No. | Chemical Structure |
| CIM-1 | |
| CIM-2 | |
| CIM-3 | |
| CIM-4 | |

TABLE A-continued

Imide-Based Addition-Fragmentation Monomers

| Cyclic imide monomers No. | Chemical Structure |
| --- | --- |
| CIM-5 | 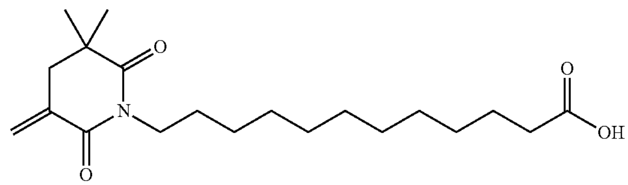 [SMILES: C=C1CC(C)(C)C(=O)N(CCCCCCCCCCCC(=O)O)C1=O] |
| CIM-6 | 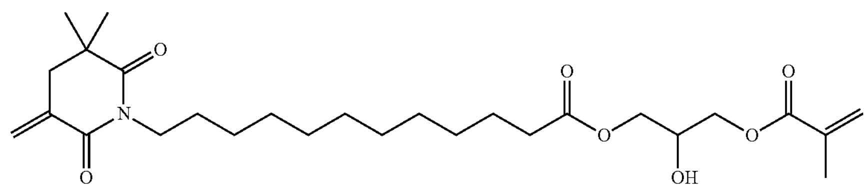 [SMILES: C=C(C)C(=O)OCC(O)COC(=O)CCCCCCCCCCCN1C(=O)C(=C)CC(C)(C)C1=O] |
| CIM-7 | 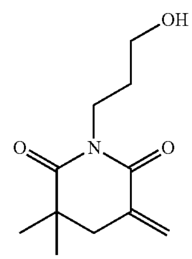 |
| CIM-8 | 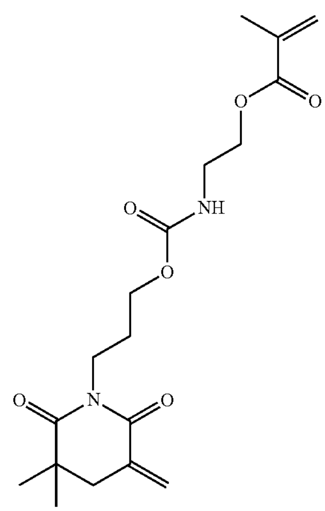 [SMILES: C=C(C)C(=O)OCCNC(=O)OCCCN1C(=O)C(=C)CC(C)(C)C1=O] |
| CIM-9 | 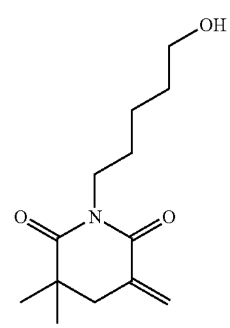 [SMILES: C=C1CC(C)(C)C(=O)N(CCCCCO)C1=O] |

TABLE A-continued
Imide-Based Addition-Fragmentation Monomers
| Cyclic imide monomers No. | Chemical Structure |
|---|---|
| CIM-10 | 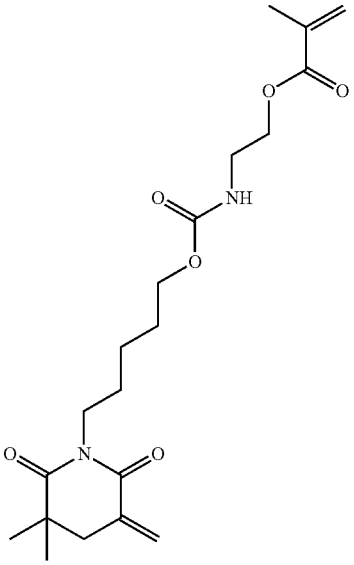 [SMILES: C=C(C)C(=O)OCCNC(=O)OCCCCCN1C(=O)C(=C)CC(C)(C)C1=O] |
| CIM-11 | 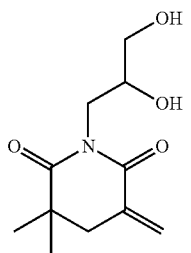 [SMILES: C=C1CC(C)(C)C(=O)N(CC(O)CO)C1=O] |
| BCIM-1 | 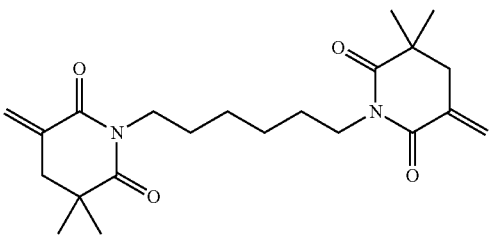 |
| BCIM-2 | 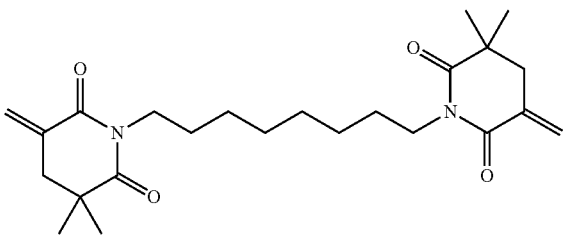 |
| BCIM-3 | 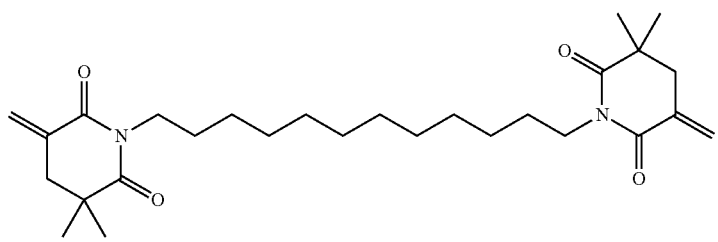 |

TABLE A-continued

Imide-Based Addition-Fragmentation Monomers

| Cyclic imide monomers No. | Chemical Structure |
|---|---|
| HBCIM | 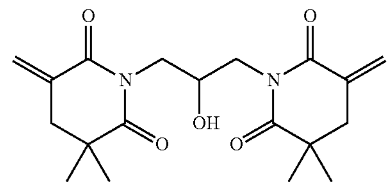 |
| MA-BCM-1 | 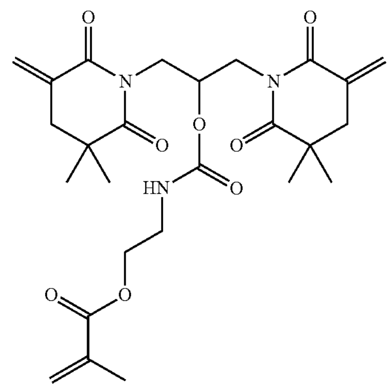 |

Although these depicted cyclic imide monomers comprise a (meth)acrylate or carboxylic acid group as a representative (e.g. free-radically polymerizable) ethylenically unsaturated groups, such monomers can alternatively have (meth)acrylamide, vinyl, styrenic or ethynyl (e.g. free-radically polymerizable) ethylenically unsaturated groups.

The molecular weight of the cyclic imide monomers is at least 150 g/mole. In typical embodiments, the molecular weight of the monomer is no greater than 1500, 1000, 750, or 500 g/mole.

Without intending to be bound by theory, it is believed that the addition-fragmentation monomer follows an addition-fragmentation pathway as shown in the following representative Reaction Scheme 1, wherein the —R bonded to the nitrogen atom is L-Y, as previously described.

Reaction Scheme 1

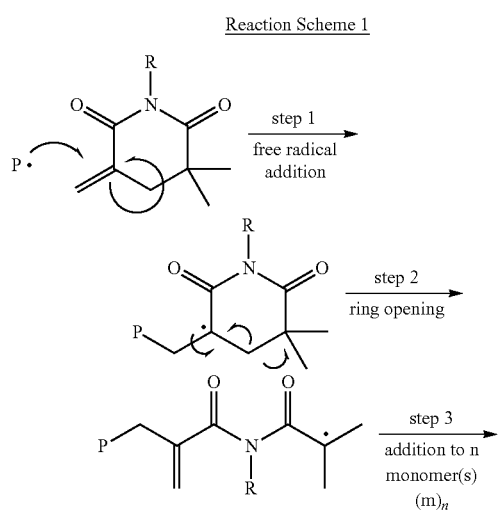

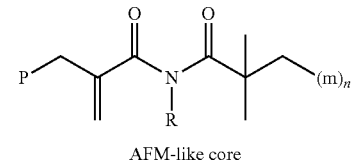

AFM-like core

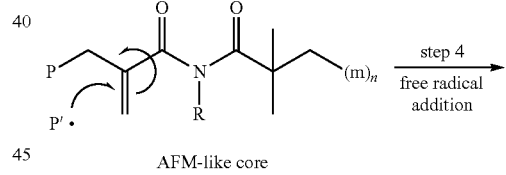

AFM-like core

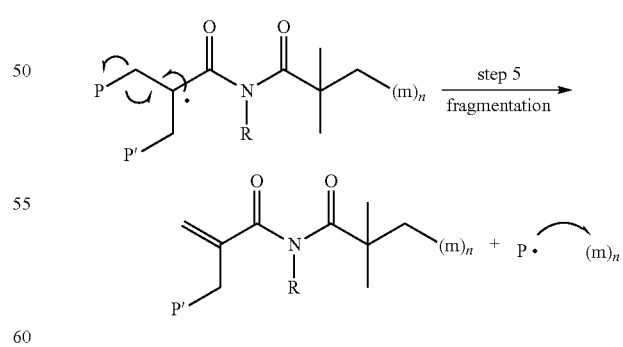

In Scheme 1, Step 1 a free-radically polymerizable ethylenically unsaturated monomer, oligomer, or polymer, represented by P•, adds to the α,β-unsaturation of the cyclic imide monomer. In Step 2, the cyclic monomer ring opens into the following linear imide radical comprising an α,β-unsaturation

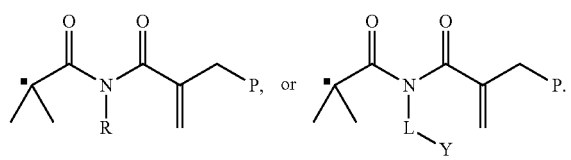

In Step 3, the α-carbonyl tertiary radical (adjacent the pendent dimethyl group) can initiate polymerization of a monomer.

In Step 4, a free-radically polymerizable ethylenically unsaturated oligomer or polymer, represented by P•, adds to the α,β-unsaturation of the cyclic imide monomer. When at least two of the P groups are polymer chains, this reaction may be characterized as crosslinking.

The crosslink can fragment as shown in Step 5 to form a stable α-carbonyl tertiary radical (represented by P•M) and a residue bearing an α,β-unsaturation. The α,β-unsaturation can undergo radical addition, as depicted in Step 4, that can subsequently fragment, as depicted in Step 5. Thus, Steps 4 and 5 can be repeated to further relieve polymerization stress.

As shown in Reaction Scheme 1, the addition-fragmentation cyclic imide comprising an α,β-unsaturation monomer, but lacking an additional ethylenically unsaturated polymerizable group provides several mechanisms for stress relief. Further, stress relief may also be a result of slower cure rates in the presence of the cyclic imide addition-fragmentation monomers, delaying the gel point. Post-gel shrinkage is a major component in stress development; therefore, delaying the gel point even slightly may lead to stress relief by allowing additional time for material to flow during the curing process.

In another embodiment, the imide ring structure comprises an alpha, beta-unsaturation and at least one additional (e.g. free-radically polymerizable) ethylenically unsaturated group. As depicted in the following Reaction Scheme 2, such cyclic imide monomer can provide all the same polymer and monomer additions as well as ring-opening and chain cleavage fragmentations as depicted in Reaction Scheme 1. In this embodiment, the additional ethylenically unsaturated group can also polymerize, or in other words crosslink.

Reaction Scheme 2
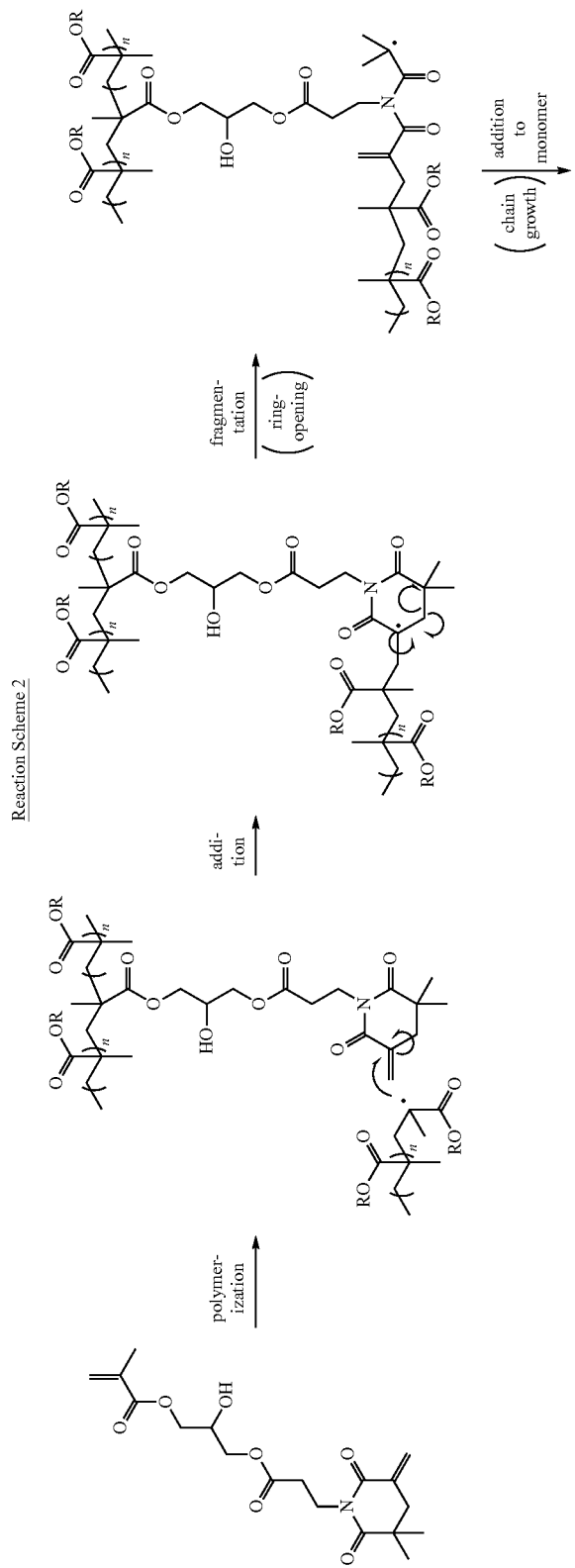

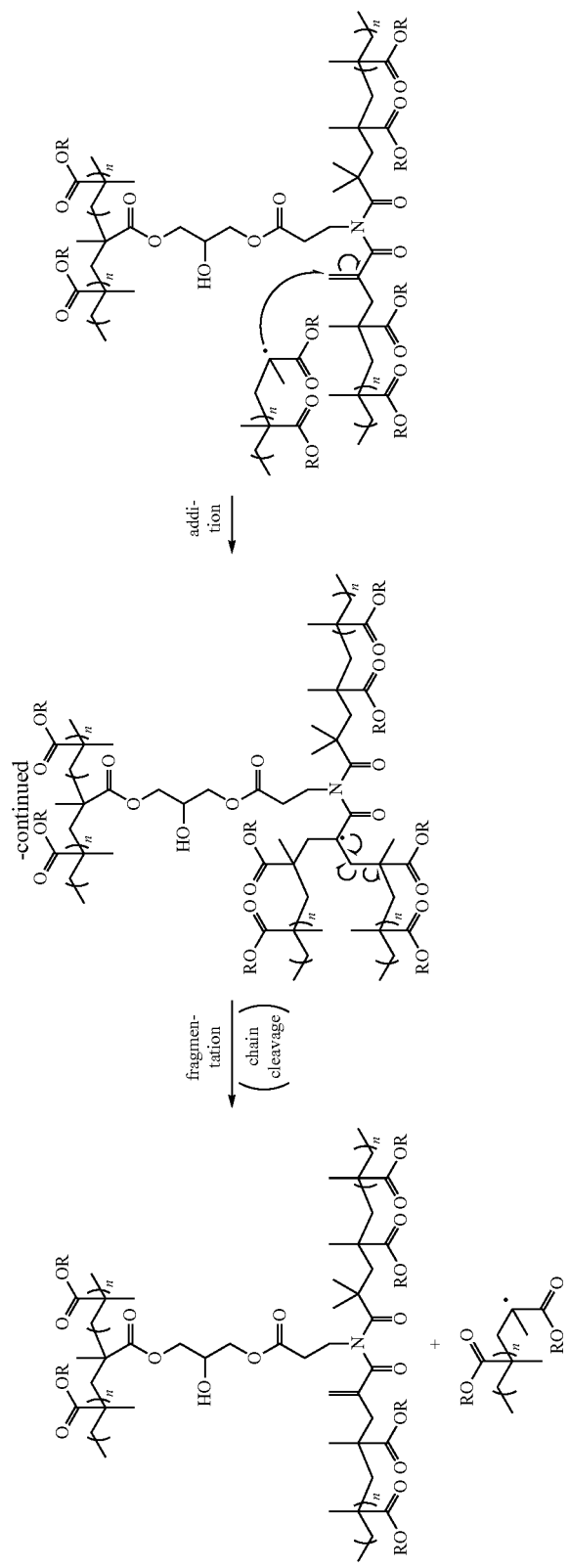

Although Reaction Scheme 2 is depicted with a cyclic imide monomer having a specific -L-Y group bonded to the nitrogen atom, the cyclic imide monomer may comprise other -L-Y groups as described herein.

In another embodiment, the cyclic imide monomer comprises at least two imide ring structures that comprise an $\alpha,\beta$-unsaturation. As depicted in the following Reaction Scheme 3, such cyclic imide monomer can provide all the same polymer and monomer additions as well as ring-opening and chain cleavage fragmentations as depicted in Reaction Scheme 1. In the following Reaction Scheme 3, both imide ring structures are depicted as concurrently ring opening following by concurrent monomer addition. However, such addition and fragmentation reactions can also occur sequentially or in other words, each ring can react independently. Further, the R group may comprise an additional pendent (e.g. free radically polymerizable) ethylenically unsaturated group -L-Y, as will subsequently be described. In this embodiment, the cyclic imide can also polymerize, or in other words crosslink as depicted in Reaction Scheme 2.

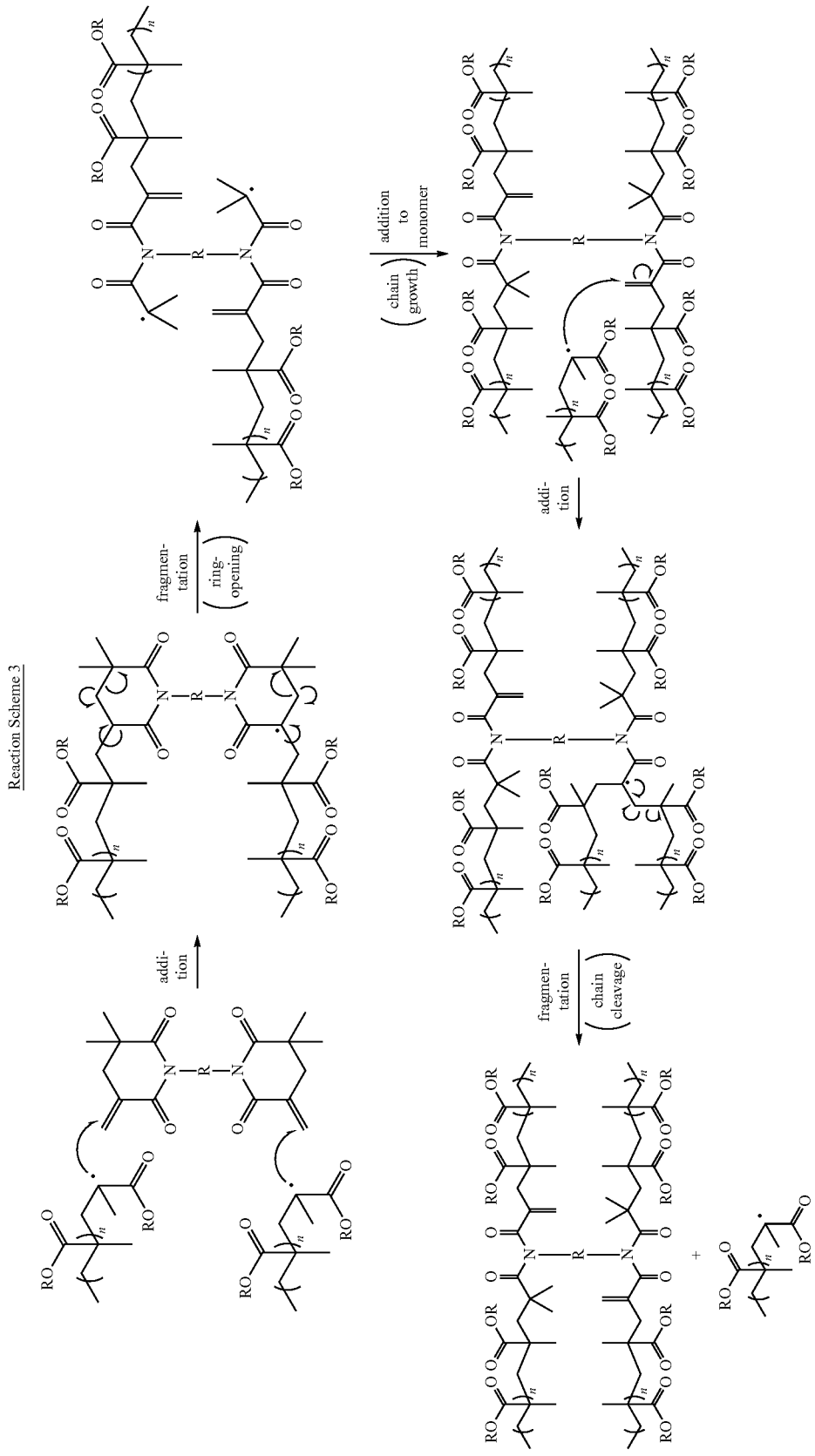
Reaction Scheme 3

Although Reaction Schemes 1-3 are depicted with a specific 6-membered cyclic imide monomer, other cyclic imide monomers comprising at least 6 covalently bonded atoms and an α,β-unsaturation would follow the same or similar addition-fragmentation pathway.

In one embodiment, a method of preparing a cyclic imide monomer comprising an α, β-unsaturated carbonyl is described. The method comprises reacting a dicarboxylic acid comprising an α, β-unsaturated carbonyl with a dehydrating agent forming a cyclic compound comprising an anhydride group and an α, β-unsaturated carbonyl; and reacting the anhydride group with a compound comprising an amine group and a unreactive group such as alkyl or aryl or a reactive group such as carboxylic acid or hydroxyl group forming a cyclic compound comprising an α, β-unsaturated carbonyl and an imide group.

One representative dicarboxylic acid is 2,2,-dimethyl-4-methylidenepentanedioic acid, as previously described. Other dicarboxylic acids can be utilized provided that the dicarboxylic acids comprises at least three contiguous carbon atoms bearing an α, β-unsaturated carbonyl between the acid groups, as previously described.

Suitable dehydrating agents including acid anhydrides such as acetic anhydride and trifluoroacetic anhydride; phosphorus-based dehydrating agents such as phosphorus pentachloride or phosphorus pentoxide, carbodiimide-based dehydrating agents such as dicyclohexylcarbodiimide.

Representative compounds comprising a (e.g. primary) amine group and an alkyl or aryl terminal group include 4-aminostyrene, butyl amine, pentyl amine, hexyl amine, phenethylamine and benzyl amine.

A representative reaction scheme is as follows:

Reaction Scheme 4

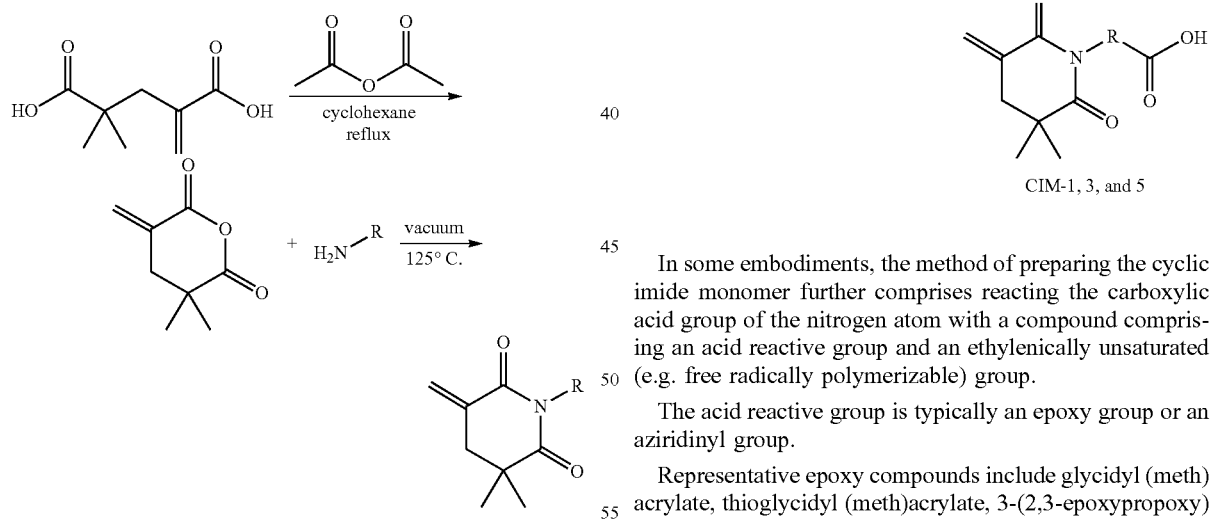

Suitable (e.g. aliphatic) compounds comprising an amine group and a carboxylic acid group typically comprise a primary amine group bonded to a terminal acid group by means of an alkylene linking group. The alkylene linking group typically comprises 2-12 carbon atoms. Representative examples include for example 3-aminopropanoic acid, 4-aminobutanoic acid, 3-aminobutanoic acid, 2-aminobutanoic acid, 5-aminopentanoic acid, 2-aminopentanoic acid, 3-aminopentanoic acid, 4-aminopentanoic acid, 6-aminohexanoic acid, 2-aminohexanoic acid, 3-aminohexanoic acid, 4-aminohexanoic acid, 5-aminohexanoic acid, 7-aminoheptanoic acid, 6-aminoheptanoic acid, 5-aminoheptanoic acid, 4-aminoheptanoic acid, 3-aminoheptanoic acid, 2-aminoheptanoic acid, 8-aminooctanoic acid, 7-aminooctanoic acid, 6-aminooctanoic acid, 5-aminooctanoic acid, 4-aminooctanoic acid, 3-aminooctanoic acid, 2-aminoocatanoic acid, 6-amino caproic acid, and 12-aminododecanoic acid. Other suitable compounds comprising an amine group and a carboxylic acid group include (e.g. naturally occurring) amino acids such as glycine, alanine, valine, isoleucine, leucine, methionine, cysteine, phenylalanine, serine (also has an alcohol), threonine (alcohol as well), tyrosine, tryptophan, asparagine, glutamine, glutamic acid, and aspartic acid, histidine, arginine, or lysine.

A representative reaction scheme is as follows:

Reaction Scheme 5

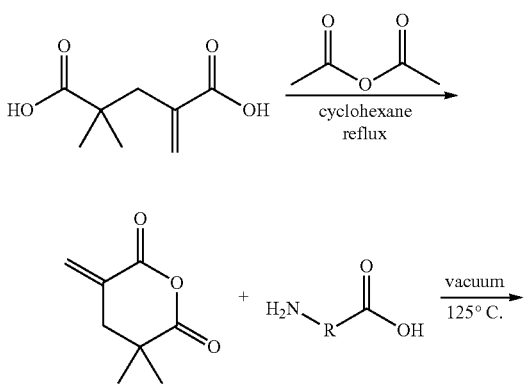

CIM-1, 3, and 5

In some embodiments, the method of preparing the cyclic imide monomer further comprises reacting the carboxylic acid group of the nitrogen atom with a compound comprising an acid reactive group and an ethylenically unsaturated (e.g. free radically polymerizable) group.

The acid reactive group is typically an epoxy group or an aziridinyl group.

Representative epoxy compounds include glycidyl (meth)acrylate, thioglycidyl (meth)acrylate, 3-(2,3-epoxypropoxy)phenyl (meth)acrylate, 2-[4-(2,3-epoxypropoxy)phenyl]-2-(4-(meth)acryloyloxy-phenyl)propane, 4-(2,3-epoxypropoxy)cyclohexyl (meth)acrylate, 2,3-epoxycyclohexyl (meth)acrylate, 3,4-epoxycyclohexyl (meth)acrylate, and 4-hydroxybutylacrylate glycidyl ether.

Representative aziridinyl compounds include N-(meth)acryloylaziridine, 2-(1-aziridinyl)ethyl (meth)acrylate, 4-(1-aziridinyl)butyl acrylate, 2-[2-(1-aziridinyl)ethoxy]ethyl (meth)acrylate, 2-[2-(1-aziridinyl)ethoxycarbonylamino]ethyl (meth)acrylate, 12-[2-(2,2,3,3-tetramethyl-1-aziridinyl)ethoxycarbonylamino]dodecyl (meth)acrylate, and 1-(2-propenyl)aziridine.

A representative reaction scheme is as follows:

Reaction Scheme 6

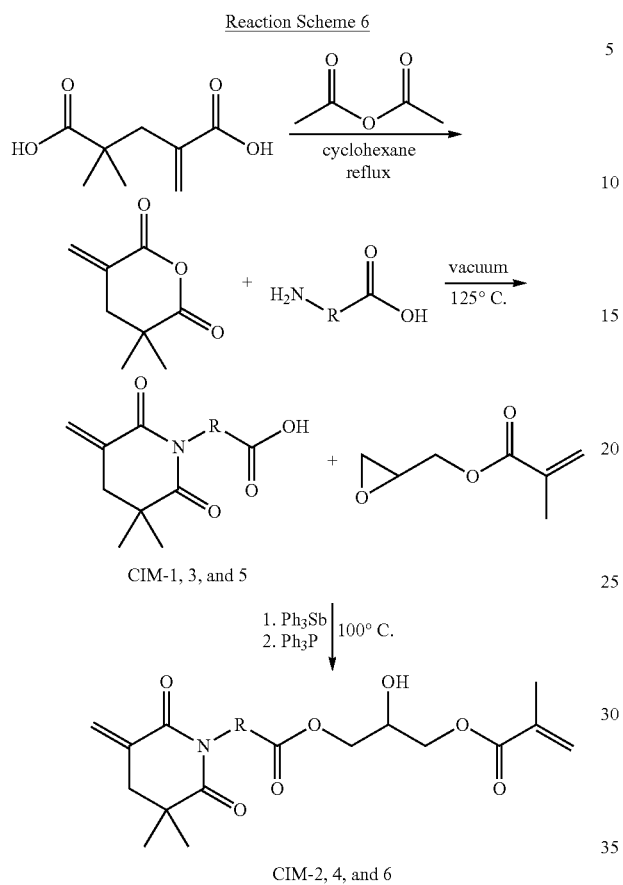

CIM-1, 3, and 5

CIM-2, 4, and 6

The reaction of carboxylic acid with aziridinyl compounds is depicted in WO2012/112304.

Suitable compounds comprising an amine group and one or more hydroxyl groups including diols. Representative compounds include for example 3-amino-1-propanol, 5-amino-1-pentanol, 3-amino-1,2-propanediol.

The cyclic imide compounds having a hydroxyl group can be reacted with a compound comprising an isocyanate group and a (meth)acrylate group. Representative isocyanate compounds include 2-isocyanatoethyl (meth)acrylate, 3-isocyanatopropyl (meth)acrylate, 4-isocyanatocyclohexyl (meth)acrylate, 4-isocyanatostyrene, 2-methyl-2-propenoyl isocyanate, 4-(2-(meth)acryloyloxyethoxycarbonylamino) phenylisocyanate, allyl 2-isocyanatoethylether, and 3-isocyanato-1-propene, 3-isocyanato-1-propyne, 3-isopropenyl-α,α-dimethylbenzyl isocyanate.

The above reaction schemes depict preparing a monomer comprising a single heterocyclic ring comprising an imide group and α, β-unsaturated carbonyl.

In other embodiments, the cyclic imide monomer comprises at least two cyclic imide groups. One suitable method for preparing a cyclic bis-imide monomer comprises reacting a dicarboxylic acid comprising an α, β-unsaturated carbonyl with a dehydrating agent forming a cyclic compound comprising an anhydride group and an α, β-unsaturated carbonyl (as previously described in Reaction Scheme 4); and reacting the anhydride group with a diamine. A representative reaction scheme is as follows:

Reaction Scheme 7

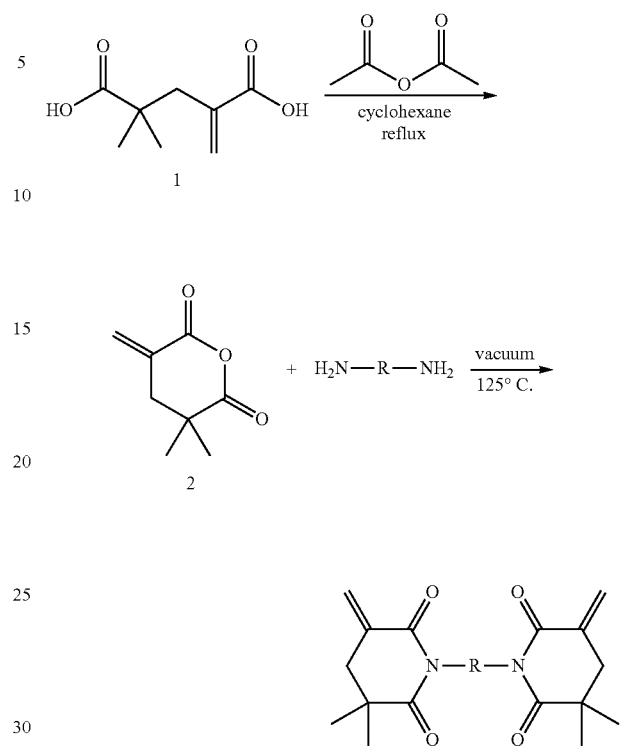

In some embodiments, the diamines is an aliphatic diamine where the amine groups are bonded with an alkylene linking group. In some embodiments, the alkylene linking group comprising 2 to 12 carbon atoms. The alkylene linking group may comprise straight-chain, branched, or cyclic moieties as well as a combination thereof. Suitable examples include ethylene diamine, 1,3-propanediamine, 1,2-propanediamine, 1,4-butanediamine, 1,2-butanediamine, 1,3-butanediamine, 1,5-pentanediamine, 1,2-pentanediamine, 1,3-pentanediamine, 1,4-pentanediamine, 2,4-pentanediamine, 1,6-hexanediamine, 1,7-heptanediamine, 1,8-octanediamine, 1,9-nonanediamine, 1,10-decanediamine, 1,12-dodecanediamine, isophorone diamine (cis and trans 5-amino-1,3,3-trimethylcyclohexanemethylamine), 1,5-diamino-2-methylpentane, trans-1,2-diaminocyclohexane, cis-1,2-diaminocyclohexane, 1,2-diphenyl-1,2-ethylenediamine, 4,4'-methylenebis(cyclohexylamine), and 4,4'methylenebis(2-methylcyclohexylamine).

In other embodiments, the diamine is an aromatic diamine wherein the amine groups are bonded with a linking group comprising an arylene moiety. The linking group typically comprises a C6 to C12 arylene group. Suitable examples include p-phenylenediamine, o-phenylenediamine, m-phenylenediamine, 4,4'-diaminobiphenyl, 4,4'-methylenedianiline.

In another embodiment, the diamine may further comprise one or more pendent reactive (e.g. hydroxyl or carboxylic acid) groups. The pendent reactive (e.g. hydroxyl group) can be reacted with a compound comprising a coreactive group and a (e.g. free-radically polymerizable) ethylenically unsaturated group, such as an isocyantoalkyl (meth)acrylate or acid reactive (meth)acrylate as previously described. Representative reaction schemes are as follows:

Reaction Scheme 8

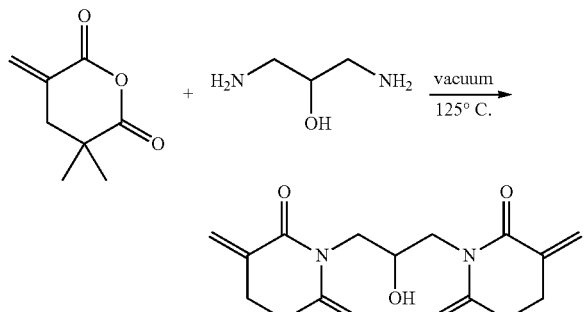

Reaction Scheme 9

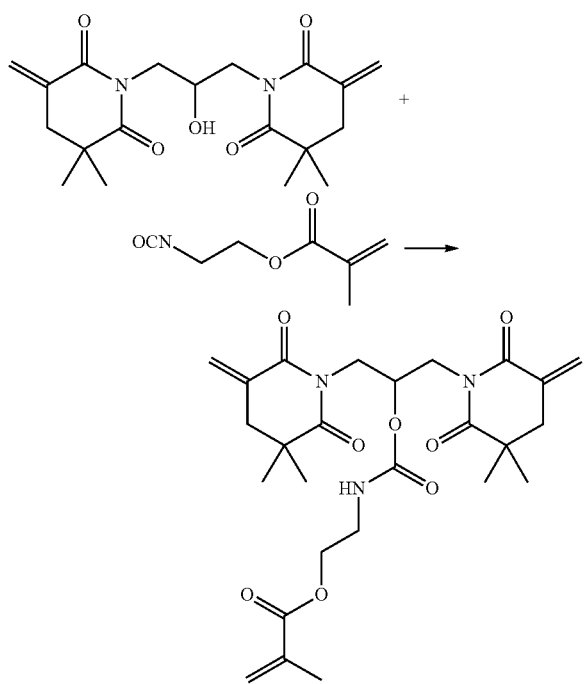

Although Reaction Schemes 4-6 are depicted with a specific 6-membered cyclic imide monomer, other cyclic imide monomers comprising at least 6 covalently bonded atoms and an α,β-unsaturation could be prepared using other dicarboxylic acids comprising an α, β-unsaturated carbonyl.

In some embodiments, a polymerizable composition is described comprising at least one addition-fragmentation cyclic imide monomer, as described herein. The addition-fragmentation monomer of the polymerizable composition comprises at least one cyclic imide monomer as described herein. The polymerizable composition may have a single cyclic imide monomer, a combination of two or more cyclic imide monomers, or at least one cyclic imide monomer in combination with a different addition-fragmentation monomer, such as described in WO2012/112304.

The polymerizable composition typically comprises addition-fragmentation monomer(s) in an amount of at least 0.005, 0.006, 0.007, 0.008, 0.009, or 0.01, wt. %, based on the total weight of polymerizable monomer(s), oligomer(s), and polymer(s). In some embodiments, the amount of addition-fragmentation monomer(s) is at least 0.02, 0.03, 0.04, 0.05, 0.06, 0.07, 0.08, 0.09, or 1.0 wt. %, based on the total weight of polymerizable monomer(s), oligomer(s), and polymer(s). The amount of addition-fragmentation monomer(s) is typically no greater than 10 wt. %, based on the total weight of polymerizable monomer(s), oligomer(s), and polymer(s). In some embodiments, the amount of addition-fragmentation monomer(s) is typically no greater than 9, 8, 7, 6, 5, 4, 3, 2, 1, or 0.5 wt. %, based on the total weight of polymerizable monomer(s), oligomer(s), and polymer(s). Typically, the polymerizable composition comprises the minimum amount of addition-fragmentation monomer(s) that reduces or eliminates the polymerization-based stress. Excess addition-fragmentation cyclic imide monomer(s) can reduce the mechanical properties of the polymerized composition.

In some embodiments, the curable component of the present disclosure may optionally include one or more additional addition-fragmentation agents. The addition-fragmentation agent may include at least one ethylenically unsaturated terminal group and a backbone unit comprising an α, β-unsaturated carbonyl. The addition-fragmentation agent may be free-radically cleavable.

In some embodiments, the addition-fragmentation agents may have the following structural formula:

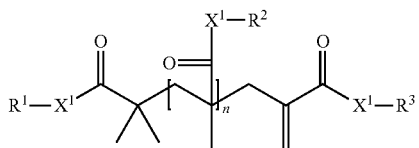

Formula I wherein
R$^1$, R$^2$ and R$^3$ are each independently Z$_m$-Q-, a (hetero)alkyl group or a (hetero)aryl group with the proviso that at least one of R$^1$, R$^2$ and R$^3$ is Z$_m$-Q-,
Q is a linking group have a valence of m+1;
Z is an ethylenically unsaturated polymerizable group,
m is 1 to 6, preferably 1 to 2;
each X$^1$ is independently —O— or —NR$^4$—, where R$^4$ is H or C$_1$-C$_4$ alkyl, and
n is 0 or 1.

Addition-fragmentation agents according to Formula I are described in U.S. Pat. No. 9,403,966 which is incorporated herein by reference in its entirety.

For embodiments wherein the addition fragmentation agents are multifunctional, comprising at least two ethylenically unsaturated group (e.g. Z is ≥2 in Formula I), the material can function as crosslinking agents, where the crosslinks are labile.

The ethylenically unsaturated moiety, Z, of the monomer may include, but is not limited to the following structures, including (meth)acryloyl, vinyl, styrenic and ethynyl, that are more fully described in reference to the preparation of the compounds below.

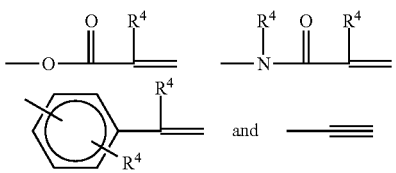

Wherein each $R^4$ is independently H or $C_1$-$C_4$ alkyl

In some embodiments, Q is selected from —O—, —S—, —$NR^4$—, —$SO_2$—, —$PO_2$—, —CO—, —OCO—, —$R^6$—, —$NR^4$—CO— $NR^4$—, $NR^4$—CO—O—, $NR^4$—CO—$NR^4$—CO—O—$R^6$—, —CO—$NR^4$—$R^6$—, —$R^6$—CO—O—$R^6$—, —O—$R^6$—, —S—$R^6$—, —$NR^4$—$R^6$—, —$SO_2$—$R^6$—, —$PO_2$—$R^6$—, —CO—$R^6$—, —OCO—$R^6$—, —$NR^4$—CO—$R^6$—, $NR^4$—$R^6$—CO—O—, and $NR^4$—CO—$NR^4$—, wherein each $R^4$ is hydrogen, a $C_1$ to $C_4$ alkyl group, or aryl group, each $R^6$ is an alkylene group having 1 to 6 carbon atoms, a 5- or 6-membered cycloalkylene group having 5 to 10 carbon atoms, or a divalent arylene group having 6 to 16 carbon atoms, with the proviso that Q-Z does not contain peroxidic linkages.

In some embodiments, Q is an alkylene, such as of the formula —$C_rH_{2r}$—, where r is 1 to 10. In other embodiments, Q is a hydroxyl-substituted alkylene, such as —$CH_2$—CH(OH)—$CH_2$—. In some embodiments, Q is an aryloxy-substituted alkylene. In some embodiments, $R^5$ is an alkoxy-substituted alkylene.

$R^1$—$X^1$— groups (and optionally $R^2$—$X^2$— groups) is typically selected from $H_2C$=C($CH_3$)C(O)—O—$CH_2$—CH(OH)—$CH_2$—O—, $H_2C$=C($CH_3$)C(O)—O—$CH_2$—CH(O—(O)C($CH_3$)=$CH_2$)—$CH_2$—O—, $H_2C$=C($CH_3$)C(O)—O—CH($CH_2$OPh)-$CH_2$—O—, $H_2C$=C($CH_3$)C(O)—O—$CH_2CH_2$—N(H)—C(O)—O—CH($CH_2$OPh)-$CH_2$—O—, $H_2C$=C($CH_3$)C(O)—O—$CH_2$—CH(O—(O)C—N(H)—$CH_2CH_2$—O—(O)C($CH_3$)C=$CH_2$)—$CH_2$—O—, $H_2C$=C(H)C(O)—O—($CH_2$)$_4$—O—$CH_2$—CH(OH)—$CH_2$—O—, $H_2C$=C($CH_3$)C(O)—O—$CH_2$—CH(O—(O)C—N(H)—$CH_2CH_2$—O—(O)C($CH_3$)C=$CH_2$)—$CH_2$—O—, $CH_3$—($CH_2$)$_7$—CH(O—(O)C—N(H)—$CH_2CH_2$—O—(O)C($CH_3$)C=$CH_2$)—$CH_2$—O—, $H_2C$=C(H)C(O)—O—($CH_2$)$_4$—O—$CH_2$—CH(—O—(O)C(H)=$CH_2$)—$CH_2$—O— and $H_2C$=C(H)C(O)—O—$CH_2$—CH(OH)—$CH_2$—O—, $H_2C$=C(H)C(O)—O—($CH_2$)$_4$—O—$CH_2$—CH(—O—(O)C(H)=$CH_2$)—$CH_2$—O—, and $CH_3$—($CH_2$)$_7$—CH(O—(O)C—N(H)—$CH_2CH_2$—O—(O)C($CH_3$)C=$CH_2$)—$CH_2$—O—.

The compounds of Formula I may be prepared from (meth)acrylate dimers and trimers by substitution, displacement or condensation reactions. The starting (meth)acrylate dimers and trimers may be prepared by free radical addition of a (meth)acryloyl monomer in the presence of a free radical initiator and a Cobalt (II) complex catalyst using the process of U.S. Pat. No. 4,547,323, incorporated herein by reference. Alternatively, the (meth)acryloyl dimers and trimers may be prepared using a cobalt chelate complex using the processes of U.S. Pat. No. 4,886,861 (Janowicz) or U.S. Pat. No. 5,324,879 (Hawthorne), incorporated herein by reference. In either process, the reaction mixture can contain a complex mixture of dimers, trimers, higher oligomers and polymers and the desired dimer or trimer can be separated from the mixture by distillation. Such synthesis is further described in U.S. Pat. No. 9,403,966.

In some embodiments, the curable component of the present disclosure may further include at least one ethylenically unsaturated monomer or oligomer in combination with the above discussed addition-fragmentation agents. In some embodiments, the ethylenically unsaturated monomer may be monofunctional, having a single (e.g. terminal) ethylenically unsaturated group. In other embodiments, such as dental restorations, the ethylenically unsaturated monomer may be multifunctional. The phrase "multifunctional ethylenically unsaturated" means that the monomers each comprise at least two ethylenically unsaturated (e.g. free radically) polymerizable groups, such as (meth)acrylate groups.

In some embodiments, such ethylenically unsaturated group is a (e.g. terminal) free radically polymerizable group including (meth)acryl such as (meth)acrylamide ($H_2C$=CHCON— and $H_2C$=CH($CH_3$)CON—) and (meth)acrylate($CH_2$CHCOO— and $CH_2C$ ($CH_3$)COO—). Other ethylenically unsaturated polymerizable groups include vinyl ($H_2C$=C—) including vinyl ethers ($H_2C$=CHOCH—). The ethylenically unsaturated terminal polymerizable group(s) may be a (meth)acrylate group, particularly for compositions that are hardened by exposure to actinic (e.g. UV) radiation. Further, methacrylate functionality may be present over the acrylate functionality in curable dental compositions.

The ethylenically unsaturated monomer may comprise various ethylenically unsaturated monomers, as known in the art, for use in dental compositions.

In some embodiments, the (e.g. dental) curable component may include one or more ethylenically unsaturated (e.g. (meth)acrylate) low volume shrinkage monomer. In some embodiments, curable compositions useful as (e.g. filled) dental compositions (useful for restorations such as fillings and crowns) may include one or more low volume shrinkage monomers such that the composition exhibits a Watts Shrinkage of less than about 4% or less than about 2%. In some embodiments, the Watts Shrinkage is no greater than 1.90%, or no greater than 1.80%, or no greater than 1.70%, or no greater than 1.60%. In some embodiments, the Watts Shrinkage is no greater than 1.50%, or no greater than 1.40%, or no greater than 1.30%, and in some embodiments no greater than 1.25%, or no greater than 1.20%, or no greater than 1.15%, or no greater than 1.10%.

The ethylenically unsaturated monomers of the curable component are typically stable liquids at about 25° C. meaning that the monomers do not substantially polymerize, crystallize, or otherwise solidify when stored at room temperature (about 25° C.) for a typical shelf life of at least 30, 60, or 90 days. The viscosity of the monomers typically does not change (e.g. increase) by more than 10% of the initial viscosity.

In some embodiments, curable compositions useful as (e.g. filled) dental compositions (useful for restorations such as fillings and crowns) may include ethylenically unsaturated monomers generally having a refractive index of at least 1.50. In some embodiments, the refractive index is at least 1.51, 1.52, 1.53, or greater. The inclusion of sulfur atoms and/or the present of one or more aromatic moieties can raise the refractive index (relative to the same molecular weight monomer lacking such substituents).

In some embodiments, the (unfilled) curable component may include solely one or more low shrink monomers in combination with the addition fragmentation agent(s). In other embodiments, the (unfilled) curable component may include a small concentration of other monomer(s). By "other" is it meant an ethylenically unsaturated monomer such as a (meth)acrylate monomer that is not a low volume shrinkage monomer. The concentration of such other monomer(s) is typically no greater than 20 wt-%, 19 wt-%, 18 wt-%, 17 wt-%, 16 wt-%, or 15 wt-% of the (unfilled) curable component. The concentration of such other monomers is typically no greater than 5 wt-%, 4 wt-%, 3 wt-%, or 2 wt-% of the filled curable component.

In some embodiments, the low volume shrinkage monomers may include isocyanurate monomers, such as described in U.S. Pat. No. 9,237,990; tricyclodecane monomers, such as described in EP Application No. 10168240.9, filed Jul. 2, 2010; polymerizable compounds having at least one cyclic allylic sulfide moiety such as described in US2008/0194722; methylene dithiepane silanes as described in U.S. Pat. No. 6,794,520; oxetane silanes such as described in U.S. Pat. No. 6,284,898; and di-, tri, and/or tetr-(meth)acryloyl-containing materials such as described in WO2008/082881; each of which are incorporated herein by reference in their entirety.

In some embodiments, the majority of the (e.g. unfilled) curable component includes one or more low volume shrinkage monomers. For example, at least 50%, 60%, 70%, 80%, 90% or more of the (e.g. unfilled) curable component may include low volume shrinkage monomer(s).

In some embodiment, the curable component may include at least one isocyanurate monomer. The isocyanurate monomer may comprise a trivalent isocyanuric acid ring as an isocyanurate core structure and at least two ethylenically unsaturated (e.g. free radically) polymerizable groups bonded to at least two of the nitrogen atoms of the isocyanurate core structure via a (e.g. divalent) linking group. The linking group is the entire chain of atoms between the nitrogen atom of the isocyanurate core structure and the terminal ethylenically unsaturated group. The ethylenically unsaturated (e.g. free radically) polymerizable groups are generally bonded to the core or backbone unit via a (e.g. divalent) linking group.

The trivalent isocyanurate core structure may have the formula:

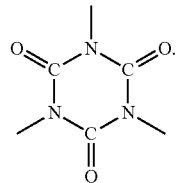

The divalent linking group may comprise at least one nitrogen, oxygen or sulfur atom. Such nitrogen, oxygen or sulfur atom forms a urethane, ester, thioester, ether, or thioether linkage. Ether and especially ester linkages can be beneficial over isocyanurate monomers comprising urethane linkages for providing improved properties such as reduced viscosity while maintaining reduced shrinkage, and/or increased mechanical properties, e.g., diametral tensile strength (DTS). Thus, in some embodiments, the divalent linking groups of the isocyanurate monomer are free of urethane linkages. In some embodiments, the divalent linking group comprises an ester linkage such as an aliphatic or aromatic diester linkage.

The isocyanurate monomer may have the general structure:

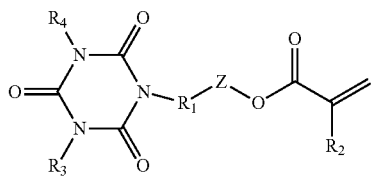

wherein $R_1$ is a straight chain, branched or cyclic alkylene, arylene, or alkarylene, optionally including a heteroatom (e.g. oxygen, nitrogen, or sulfur); $R_2$ is hydrogen or methyl; Z is alkylene, arylene, or alkarylene linking group comprising at least one moiety selected from urethane, ester, thio- ester, ether, or thioether, and combinations of such moieties; and at least one of $R_3$ or $R_4$ is

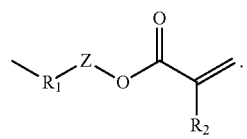

$R_1$ is typically a straight chain, branched or cyclic alkylene, optionally including a heteroatom, having no greater than 12 carbons atoms. In some favored embodiments, $R_1$ has no greater than 8, 6, or 4 carbon atoms. In some favored embodiments, $R_1$ comprises at least one hydroxyl moiety.

In some embodiments, Z comprises an aliphatic or aromatic ester linkage such as a diester linkage.

In some embodiment, Z further comprises one or more ether moieties. Hence, the linking group may comprise a combination of ester or diester moieties and one or more ether moieties.

For embodiments, wherein the isocyanurate monomer is a di(meth)acrylate monomer, $R_3$ or $R_4$ is hydrogen, alkyl, aryl, or alkaryl, optionally including a heteroatom.

$R_1$ is generally derived from the starting (e.g. hydroxy terminated) isocyanurate precursor. Various isocyanurate precursor materials are commercially available from TCI America, Portland, OR. The structures of exemplary isocyanurate precursor materials are depicted as follows:

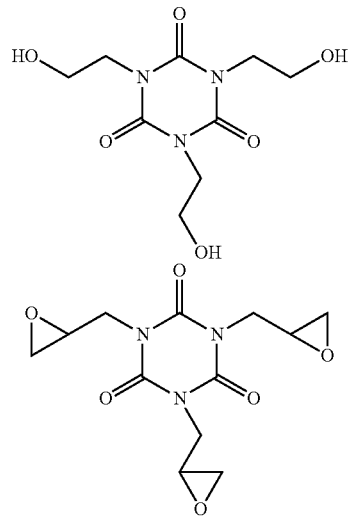

The isocyanurate (meth)acrylate monomers disclosed herein having a linking groups comprising an oxygen atom of an ester moiety may be prepared by reaction of hydroxy or epoxy terminated isocyanurates with (meth)acrylated carboxylic acids such as mono-(2-methacryloxyethyl) phthalic acid and mono-(2-methacryloxytheyl)succinic acid.

Suitable (meth)acrylated carboxylic acids include for example mono-(2-methacryloxyethyl)phthalic acid(s), mono-(2-methacryloxytheyl)succinic acid, and mono-(2-methacryloxyethyl)maleic acid. Alternatively, the carboxylic acid may comprise (meth)acrylamido functionally such as methacrylamido derivatives of naturally occurring amino acids such as methacrylamidoglycine, methacrylamidoleucine, methacrylamidoalanine etc.

In some embodiments, a single(meth)acrylated carboxylic acid is reacted with a single hydroxyl terminated isocyanurate (e.g. tris-(2-hydroxylethyl)isocyanurate). When a sufficient molar ratio of (meth)acrylate carboxylic acid is utilized such that all the hydroxyl groups of the ring are reacted, such synthesis can produce a single reaction product wherein each of the free radically terminated groups, bonded to the nitrogen atoms of the trivalent isocyanuric acid ring, are the same. However, when a single epoxy terminated isocyanurate is reacted with a single carboxylic acid, the reaction product generally comprises more than one isomer in the reaction product.

When two different hydroxy or epoxy terminated isocyanurates and/or two different (e.g. (meth)acrylated) carboxylic acids are utilized, a statistical mixture of reaction products are obtained based on the relative amounts of reactants. For example, when a mixture of a (meth)acrylated aromatic carboxylic acid and a (meth)acrylate aliphatic carboxylic acid are utilized, some of the free radically terminated divalent linking groups bonded to the nitrogen atom of the trivalent isocyanuric acid ring comprise an aromatic group, whereas others do not. Further, when a combination (e.g. 1 equivalent) of a hydroxyl terminated carboxylic acid and (e.g. 2 equivalents) of a monocarboxylic acid (such as octanoic acid) is reacted with a single hydroxyl terminated isocyanurate (e.g. tris-(2-hydroxylethyl)isocyanurate), a mono(meth)acrylate isocyanurate can be prepared as further described in U.S. Pat. No. 9,237,990. Such mono (meth)acrylate isocyanurate is suitable for use as a reactive diluent.

Alternatively, isocyanurate (meth)acrylate monomers having ether group containing linking groups can be synthesized. For example, in one illustrative synthesis, phthalic acid anhydride can be reacted with a mono-methacrylated di, tri, tetra or polyethylenegylcol in the presence of a catalytic amount of 4-(dimethylamino)pyridine (DMAP) and butylated hydroxytoluene inhibitor (BHT) at 95° C. for a 3-6 hours to form a mono-methaycrylated polyethyleneglycol phthalic acid mono-ester. The obtained methacrylated acid can be reacted, in acetone, with tris-(2-hydroxyethyl)isocyanurate using dicyclohexyl carbodiimide (DCC) at 0-5° C. then at room temperature. Such reaction scheme is depicted as follows:

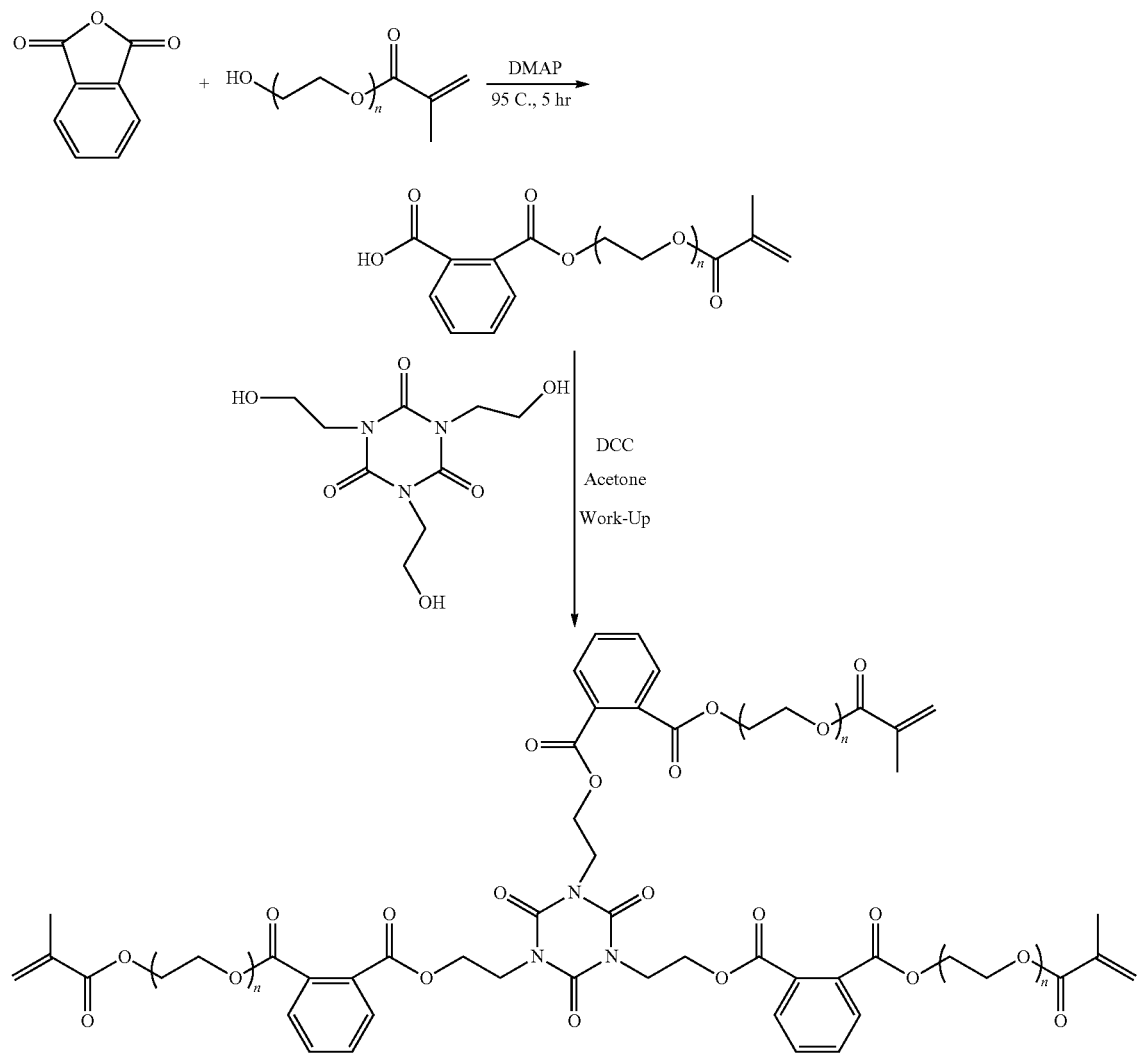

In another illustrative synthesis, tris(2-hydroxyethyl)isocyanurate can be reacted with ethylene oxide to form a polyethylene glycol terminated with a hydroxyl group. The OH termini can be esterified with meth(acrylic) acid to provide a product where the linking group is a polyether. Such reaction scheme is depicted as follows:

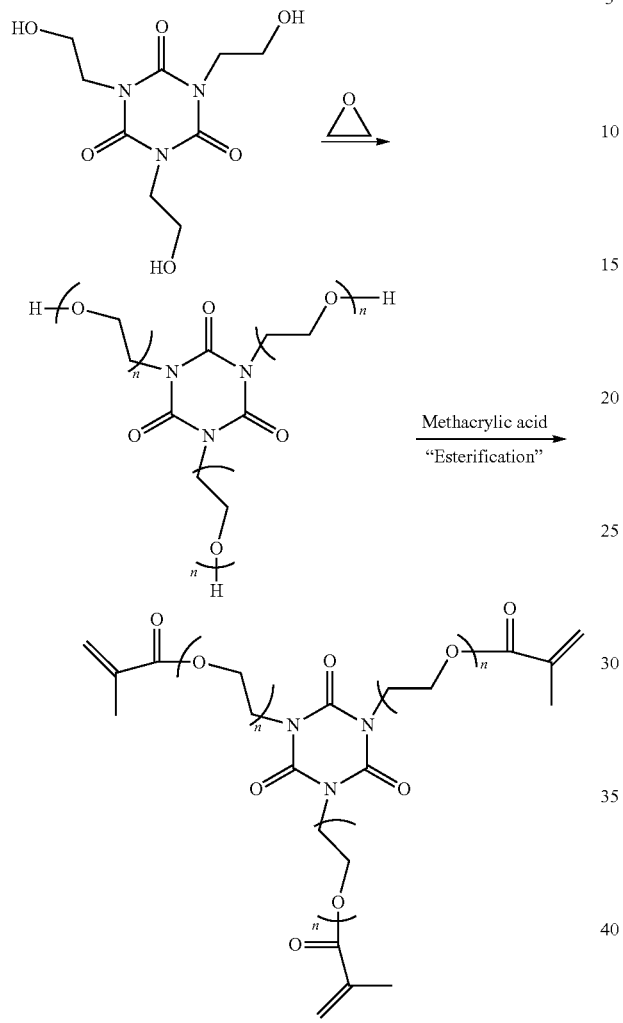

In some embodiments, the isocyanurate monomer may be a multi(meth)acrylate such as a di(meth)acrylate isocyanurate monomer or a tri(meth)acrylate isocyanurate monomer.

The di(meth)acrylate monomer may have the following structure:

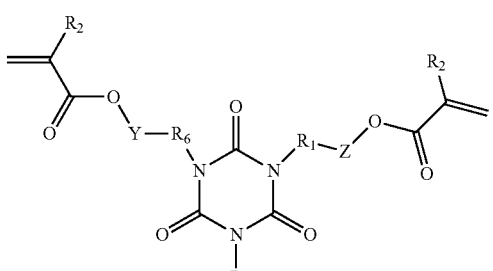

wherein $R_1$, $R_2$, $R_3$ and Z are as previously described; $R_6$ is a straight chain, branched, or cyclic alkylene, arylene, or alkarylene, optionally including a heteroatom (e.g. oxygen, nitrogen, or sulfur); and Y is alkylene, arylene, or alkarylene linking group comprising at least one moiety selected from urethane, ester, thioester, ether, or thioether, and combinations of such moieties.

Illustrative di(meth)acrylate isocyanurate monomers include:

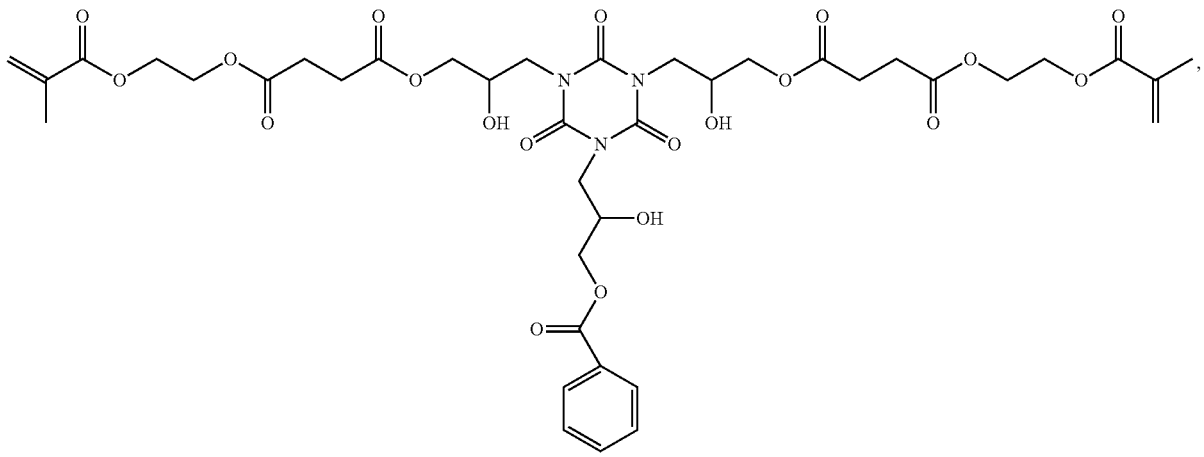

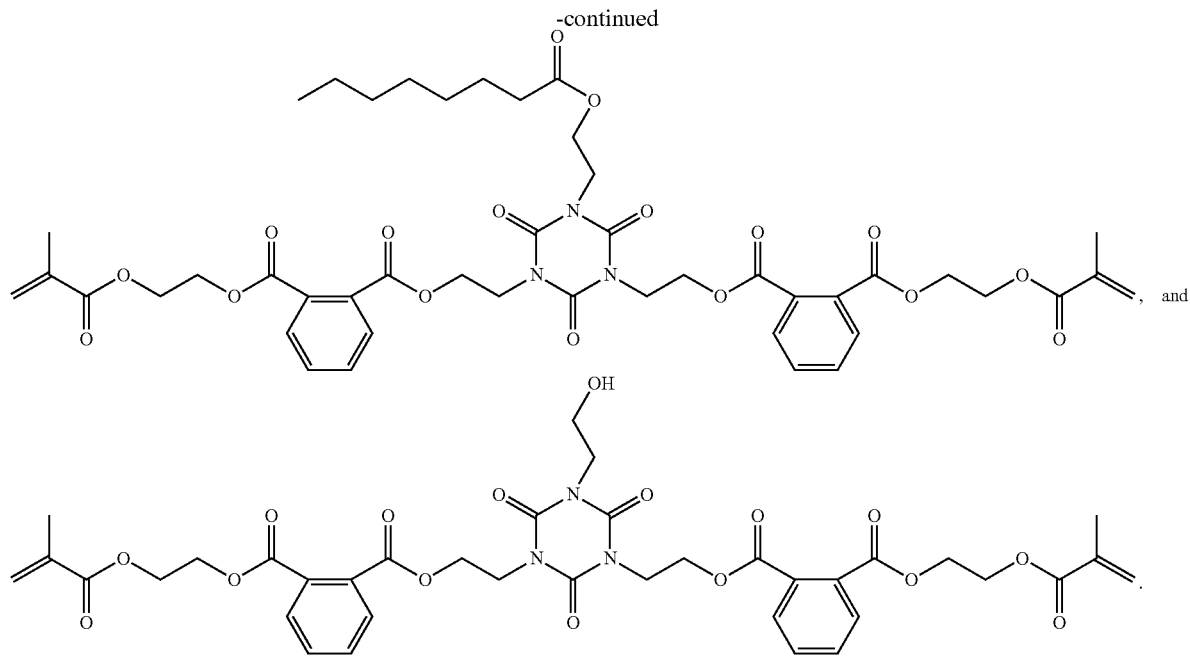

In some embodiments, the tri(meth)acrylate monomer may have the following structure:

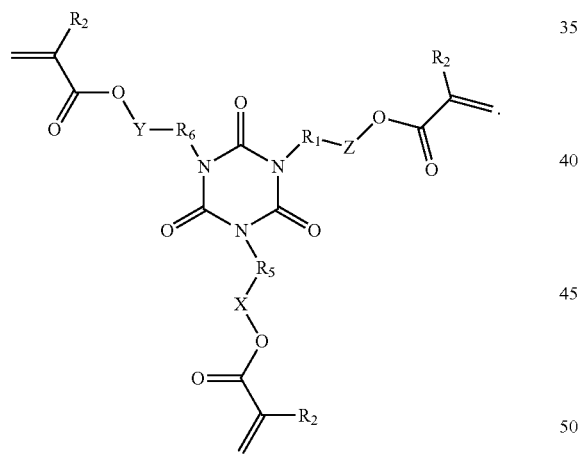

wherein $R_1$, $R_5$, and $R_6$ are independently a straight chain, branched, or cyclic alkylene, arylene, or alkarylene, optionally including a heteroatom (e.g. oxygen, nitrogen, or sulfur); $R_2$ is hydrogen or methyl; X, Y, and Z are independently alkylene, arylene, or alkarylene linking group comprising at least one moiety selected from urethane, ester, thioester, ether, thioether, or combinations of such moieties; and $R_2$ is hydrogen or methyl.

In some embodiments, $R_1$, $R_5$, and $R_6$ comprise at least one hydroxyl moiety.

Illustrative tri(meth)acrylate isocyanurate monomers include for example:

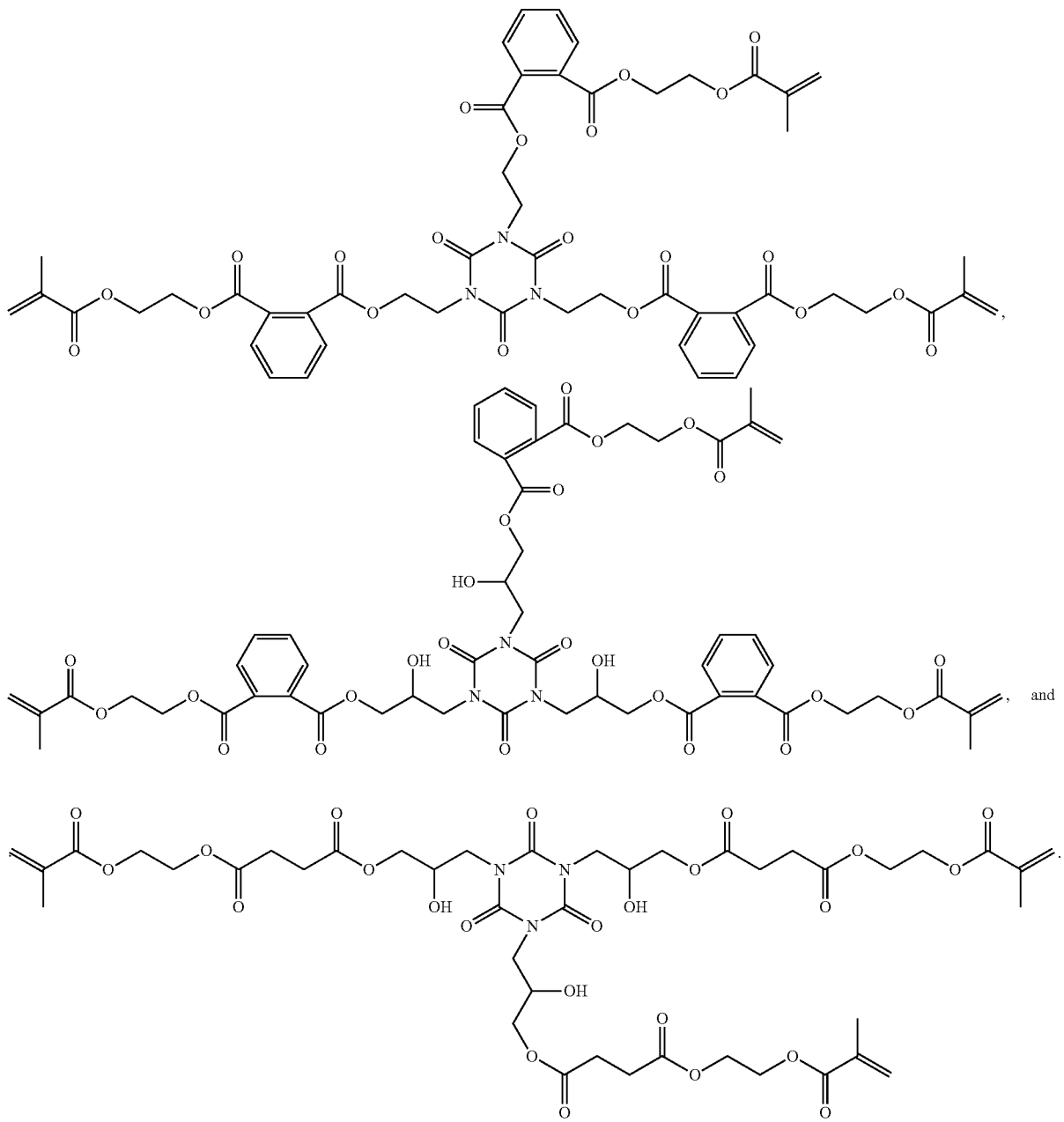

In some embodiments, the curable component may include at least one tricyclodecane monomer. The tricyclodecane monomer may comprise a single monomer or a blend of two or more tricyclodecane monomers. The concentration of multifunctional ethylenically unsaturated tricyclodecane monomer in the unfilled or filled curable component can be the same as just described for the multifunctional ethylenically unsaturated isocyanurate monomer.

In some embodiments, the curable component may include a multifunctional ethylenically unsaturated isocyanurate monomer and a multifunctional ethylenically unsaturated tricyclodecane monomer at a weight ratio ranging from about 1.5:1 to 1:1.5.

Tricyclodecane monomers may have the following core structure (i.e. backbone unit (U)):

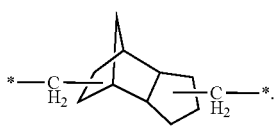

In some embodiments, the tricyclodecane monomers may have the following core structure (i.e. backbone unit (U)):

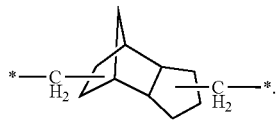

Such tricyclodecane monomers can be prepared for example from starting materials such as

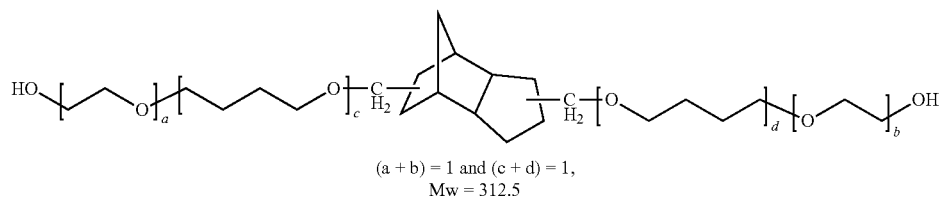

(a + b) = 1 and (c + d) = 1,
Mw = 312.5

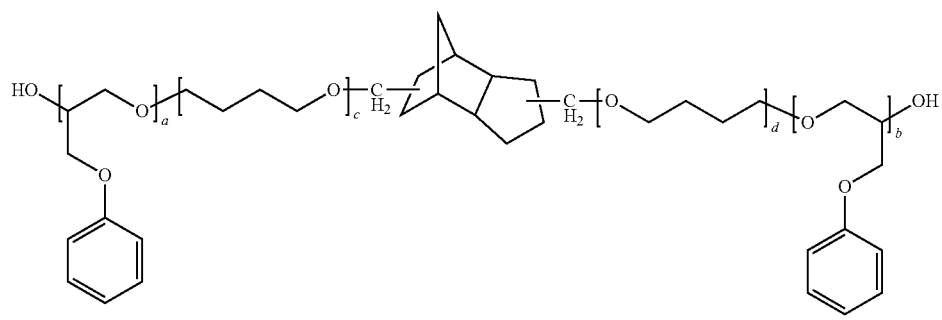

(a + b) = 1 and (c + d) = 1,
Mw = 418.6

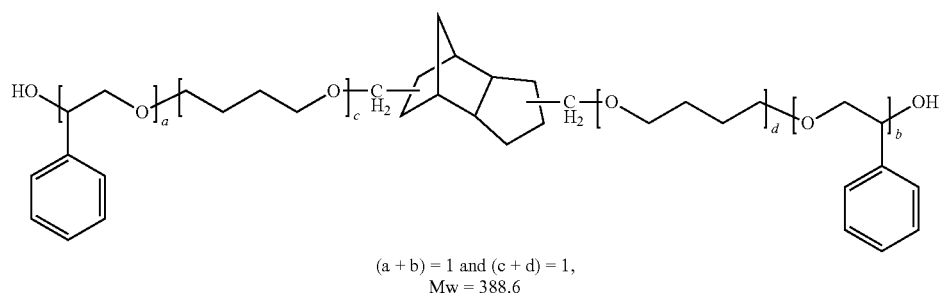

(a + b) = 1 and (c + d) = 1,
Mw = 388.6

In some embodiments, the backbone unit (U) may include one or two spacer unit(s) (S) bonded to the backbone unit (U) via an ether linkage. At least one spacer unit (S) comprises a CH(Q)-OG chain, wherein each group G comprises a (meth)acrylate moiety and Q comprises at least one group selected from hydrogen, alkyl, aryl, alkaryl and combinations thereof. In some embodiments, Q is hydrogen, methyl, phenyl, phenoxymethyl, and combinations thereof. G may be bonded to the spacer unit(s) (S) via a urethane moiety.

In some embodiments, the spacer unit(s) (S) typically comprise

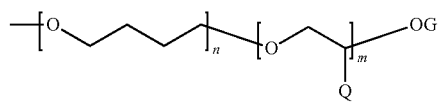

wherein m is 1 to 3; n is 1 to 3; and Q is hydrogen, methyl, phenyl, phenoxymethyl.

In other embodiments, the spacer unit(s) (S) typically comprise

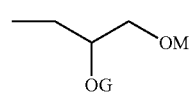

wherein M=phenyl.

In some embodiments, the tricyclodecane monomer may be characterized by the structures

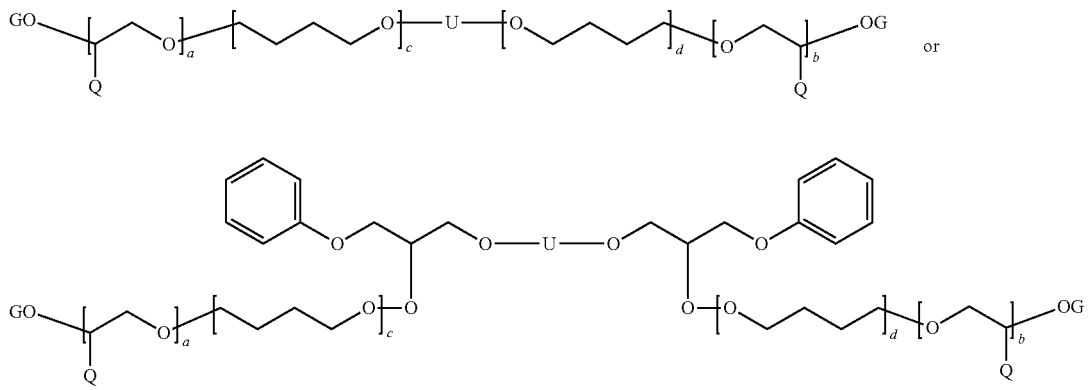

wherein for each of these tricyclodecane monomer structures a, b is 0 to 3; c, d=0 to 3; (a+b) is 1 to 6; (c+d) is 1 to 6; and Q is independently hydrogen, methyl, phenyl or phenoxymethyl.

Some illustrative species of such multifunctional ethylenically unsaturated tricyclodecane monomers are described in the following table.

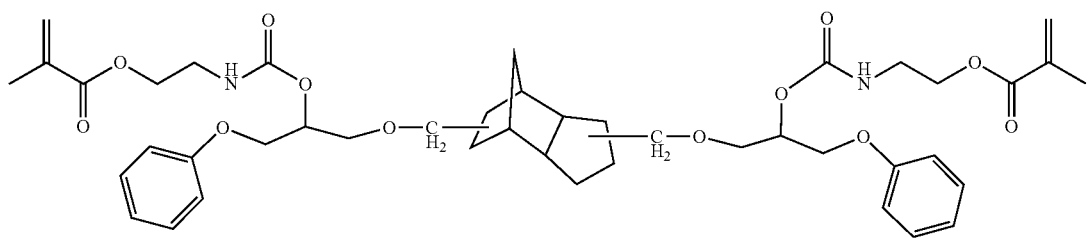

Mw = 807.0; $n_D^{20}$ = 1.531; $\eta$ = 1400 Pa*s

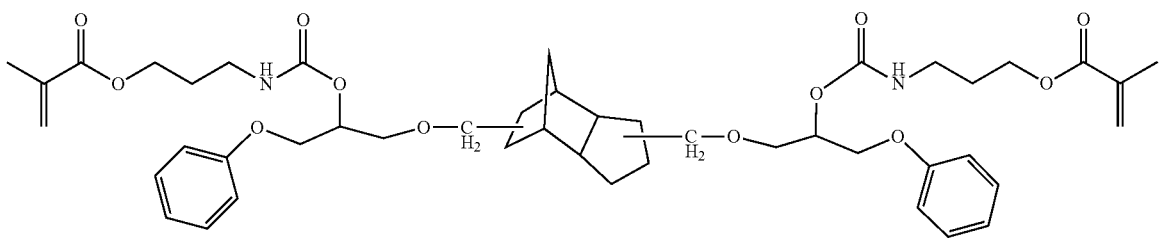

Mw = 835.1

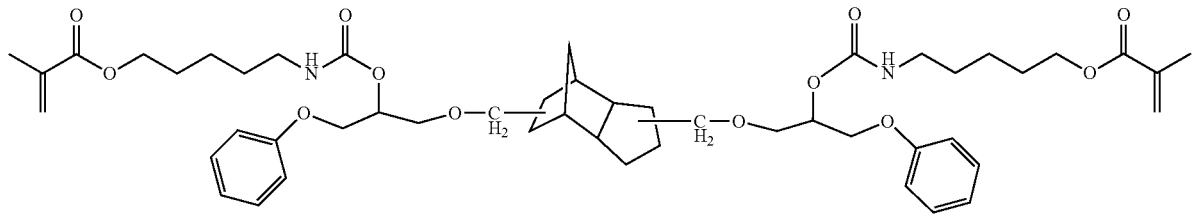

Mw = 891.2

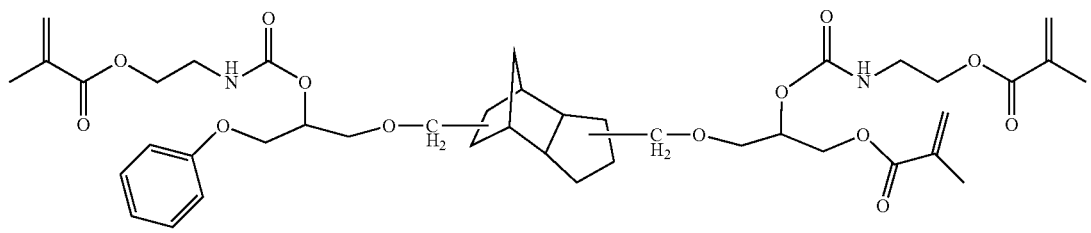
Mw = 798.9
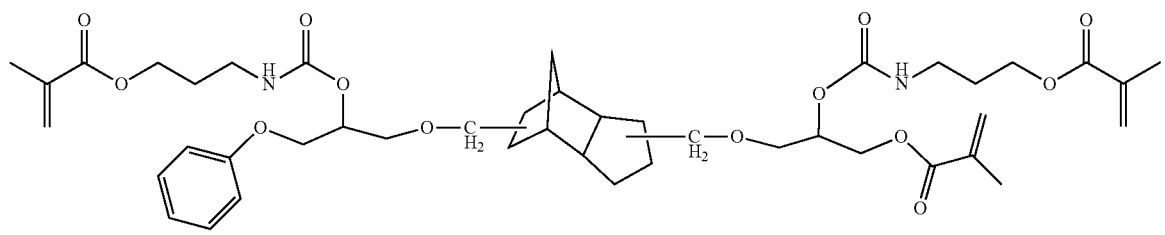
Mw = 827.0
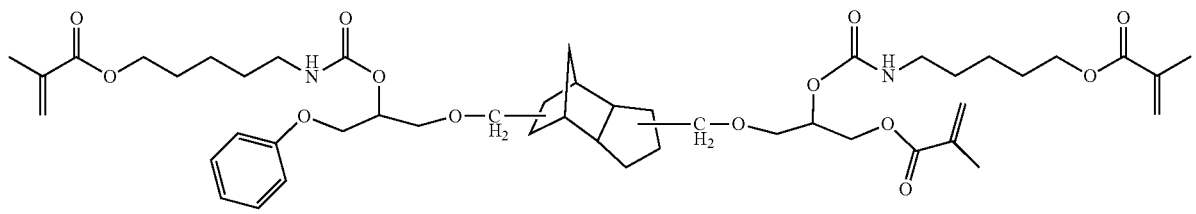
Mw = 883.1
TCD-Alcohol-IEM, reaction product of tricyclo[5.2.1.02,6]decane dimethanole (TCD-Alcohol DM) and IEM
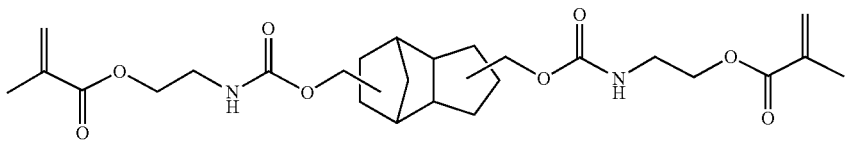
Mw = 506.6; $n_D^{20}$ = 1.510; η = 1100 Pa*s
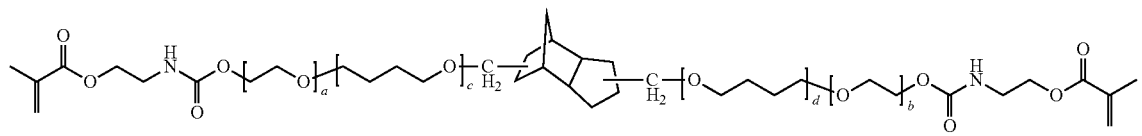
(a + b) = 1 and (c + d) = 1, Mw = 622.8; $n_D^{20}$ = 1.503; η = 45 Pa*s
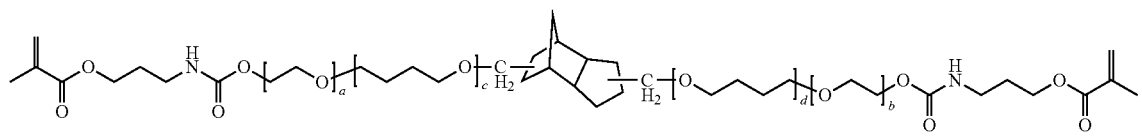
with (a + b) = 1 and (c + d) = 1, Mw = 650.9

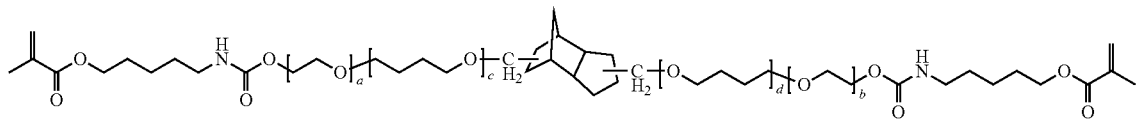
with (a + b) = 1 and (c + d) = 1, Mw = 707.0
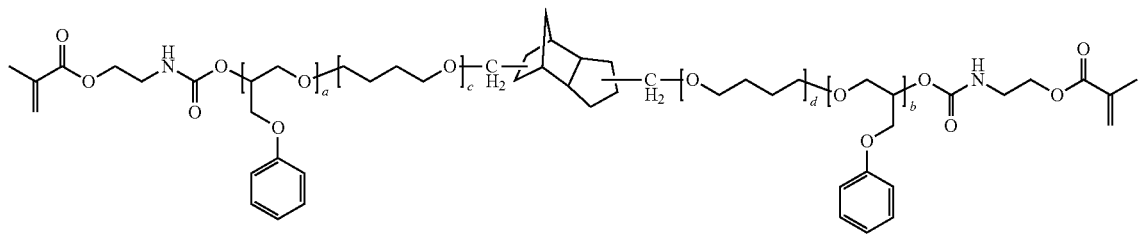
(a + b) = 1 and (c + d) = 1, Mw = 728.9; $n_D^{20}$ = 1.518; η = 433 Pa*s
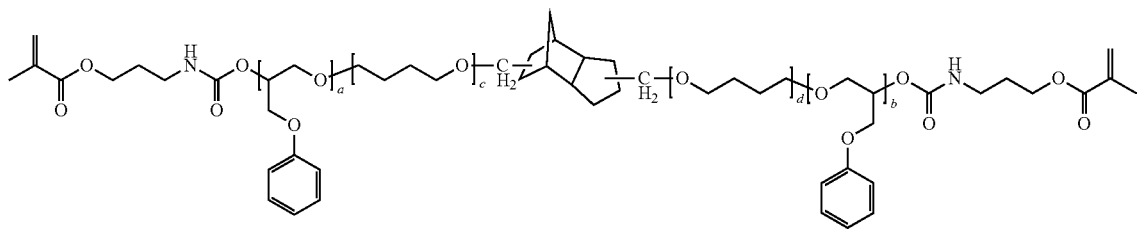
with (a + b) = 1 and (c + d) = 1, Mw = 757.0
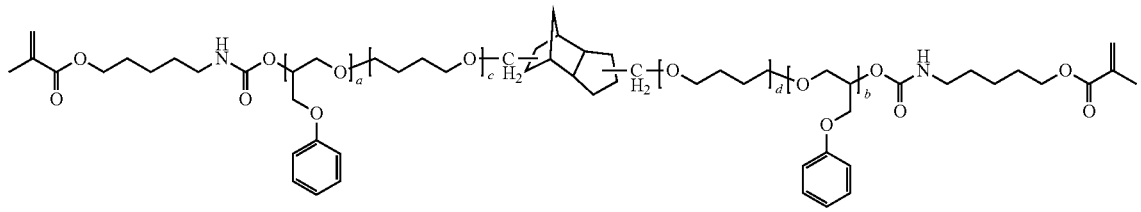
with (a + b) = 1 and (c + d) = 1, Mw = 813.1; $n_D^{20}$ = 1.513; η = 35 Pa*s
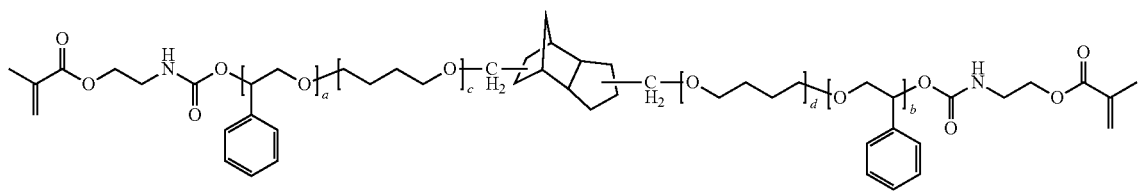
(a + b) = 1 and (c + d) = 1, Mw = 698.9
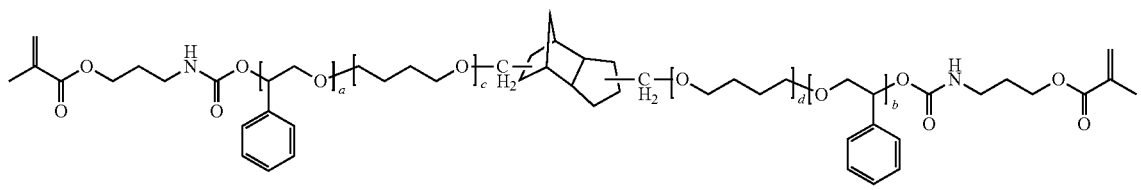
with (a + b) = 1 and (c + d) = 1, Mw = 727.0

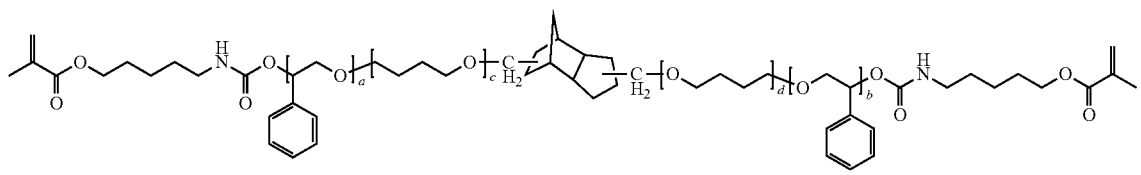

with (a + b) = 1 and (c + d) = 1, Mw = 783.1

In some embodiments, the linking groups of the isocyanurate and tricyclodecane monomers may be sufficiently low in molecular weight such that the monomer is a stable liquid at 25° C. However, the linking group(s) may be higher in molecular weight than the oxygen atom of for example 2,2-bis[4-(2-hydroxy-3-methacryloyloxypropoxy)phenyl] propane ("BisGMA"), a common monomer utilized in dental compositions, that links the (meth)acrylate group to the aromatic ring. The molecular weight of the linking group(s) of the monomers described is typically at least 50 g/mole or 100 g/mole. In some embodiments, the molecular weight of the linking group is at least 150 g/mole. The molecular weight of the linking group is typically no greater than about 500 g/mole. In some embodiments, the molecular weight of the linking group is no greater than 400 g/mole or 300 g/mole.

In some embodiments, the (i.e. calculated) molecular weight of the low shrink (e.g. isocyanurate and tricyclodecane) monomers is typically no greater than 2000 g/mole. In some embodiments, the molecular weight of the monomers is no greater than about 1500 g/mole or 1200 g/mole or 1000 g/mole. The molecular weight of the monomers is typically at least 600 g/mole.

Increasing the molecular weight without forming a solid at 25° C. can be achieved by various synthetic approaches, as depicted above. In some embodiments, the linking groups have one or more pendant substituents. For example, the linking groups may comprise one or more hydroxyl group substituents such an in the case of linking groups comprising alkoxy segments. In other embodiments, the linking groups are branched, and/or comprise at least one (i.e. aliphatic) cyclic moiety, and/or comprise at least one aromatic moiety.

In some embodiments, a by-product is formed during the synthesis of the monomer that may be a solid at about 25° C. (i.e., +/−2° C.). Such by-product is typically removed from the liquid monomer. Hence, the liquid monomer is substantially free of such solid fractions. However, it is contemplated that the liquid monomer may further comprise (e.g., non-crystalline) solid reaction by-products that are soluble in the liquid monomer.

In some embodiments, the curable component may include a polymerizable compound having at least one cyclic allylic sulfide moiety with at least one (meth)acryloyl moiety.

Such a polymerizable compound is referred to herein as a hybrid monomer or a hybrid compound. The cyclic allylic sulfide moiety may include at least one 7- or 8-membered ring that has two heteroatoms in the ring, one of which is sulfur. Most typically both of the heteroatoms are sulfur, which may optionally be present as part of an SO, SO$_2$, or S—S moiety. In other embodiments, the ring may comprise a sulfur atom plus a second, different heteroatom in the ring, such as oxygen or nitrogen. In addition, the cyclic allylic moiety may comprise multiple ring structures, i.e., may have two or more cyclic allylic sulfide moieties. The (meth)acryloyl moiety is preferably a (meth)acryloyloxy (i.e., a (meth)acrylate moiety) or a (meth)acryloylamino (i.e., a (meth)acrylamide moiety).

In some embodiments, the low shrinkage monomer may include those represented by the formulae:

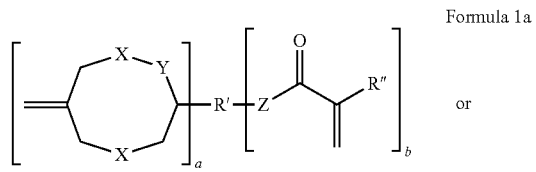

Formula 1a or

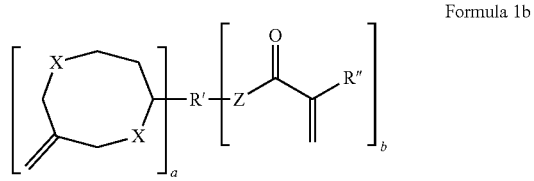

Formula 1b

In the above formulae, each X can be independently selected from S, O, N, C (e.g., CH$_2$ or CRR, where each R is independently a H or an organic group), SO, SO$_2$, N-alkyl, N-acyl, NH, N-aryl, carboxyl or carbonyl group, provided that at least one X is S or a group comprising S. Preferably, each X is S.

Y is either alkylene (e.g., methylene, ethylene, etc.) optionally including a heteroatom, carbonyl, or acyl; or is absent, thereby indicating the size of the ring, typically 7- to 10-membered rings, however larger rings are also contemplated. Preferably, the ring is either a 7- or 8-membered ring with Y thus being either absent or methylene, respectively. In some embodiments, Y is either absent or is a C1 to C3 alkylene, optionally including a heteroatom, carbonyl, acyl, or combinations thereof.

Z is O, NH, N-alkyl (straight chain or branched), or N-aryl (phenyl or substituted phenyl).

The R' group represents a linker selected from alkylene (typically having more than one carbon atom, i.e., excluding methylene), alkylene optionally including a heteroatom (e.g., O, N, S, S—S, SO, SO$_2$), arylene, cycloaliphatic, carbonyl, siloxane, amido (—CO—NH—), acyl (—CO—O—), urethane (—O—CO—NH—), and urea (—NH—CO—NH—) groups, and combinations thereof. In certain embodiments, R' comprises an alkylene group, typically a methylene or longer group, that may be either straight chain or branched, and which can be either unsubstituted, or substituted with aryl, cycloalkyl, halogen, nitrile, alkoxy, alkylamino, dialkylamino, akylthio, carbonyl, acyl, acyloxy, amido, urethane group, urea group, a cyclic allylic sulfide moiety, or combinations thereof.

R″ is selected from H, and CH$_3$, and "a" and "b" are independently 1 to 3.

Optionally, the cyclic allylic sulfide moiety can further be substituted on the ring with one or more groups selected from straight or branched chain alkyl, aryl, cycloalkyl, halogen, nitrile, alkoxy, alkylamino, dialkylamino, akylthio, carbonyl, acyl, acyloxy, amido, urethane group, and urea group. In some embodiments, the selected substituents do not interfere with the hardening reaction.

A typical low shrinkage monomer can comprise an 8-membered cyclic allylic sulfide moiety with two sulfur atoms in the ring and with the linker attached directly to the 3-position of the ring with an acyl group (i.e., Ring-OC(O)—). Typically the weight average molecular weight (MW) of the hybrid monomer ranges from about 400 to about 900 and in some embodiments is at least 250, more typically at least 500, and most typically at least 800.

Representative polymerizable compounds having at least one cyclic allylic sulfide moiety with at least one (meth)acryloyl moiety include the following

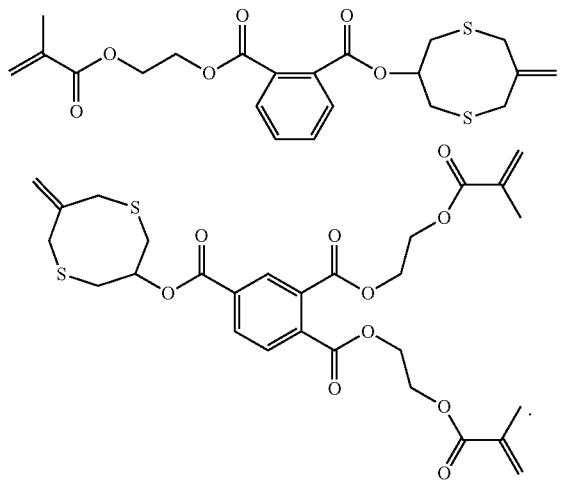

The inclusion of a polymerizable compound having at least one cyclic allylic sulfide moiety can result in a synergistic combination of low volume shrinkage in combination with high diametral tensile strength.

In some embodiments, the curable component may include a low shrinkage monomer that includes at least one di-, tri-, and/or tetra-(meth)acryloyl-containing materials having the general formula:

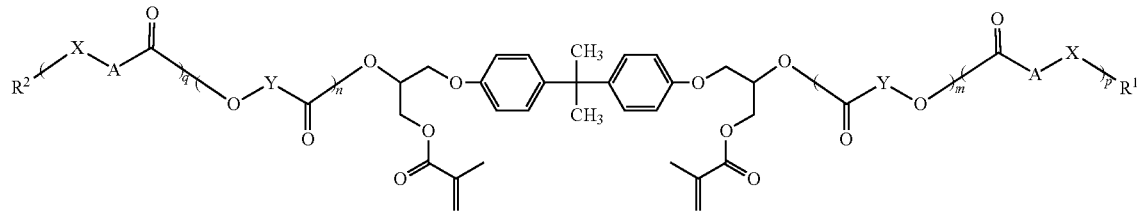

wherein: each X independently represents an oxygen atom (O) or a nitrogen atom (N); Y and A each independently represent an organic group, and R$^1$ represents —C(O)C(CH$_3$)=CH$_2$, and/or (ii) q=0 and R$^2$ represents —C(O)C(CH$_3$)=CH$_2$; m=1 to 5; n=0 to 5; p and q are independently 0 or 1; and R$^1$ and R$^2$ each independently represent H, —C(O)CH=CH$_2$, or —C(O)C(CH$_3$)=CH$_2$. In some embodiments, Y does not represent —NHCH$_2$CH$_2$— when p=0. Although, this material is a derivative of bisphenol A, when other low volume shrinkage monomer are employed, such as the isocyanurate and/or tricyclodecane monomer, the dental composition is free of (meth)acrylate monomers derived from bisphenol A.

In some embodiments, the multifunctional low shrink monomers (e.g., isocyanurate and tricyclodecane) may be (e.g., highly) viscous liquids at about 25° C., yet are flowable. The viscosity as can be measured with a Haake RotoVisco RV1 device, as described in EP Application No. 10168240.9, filed Jul. 2, 2010 is typically at least 300, or 400, or 500 Pa*s and no greater than 10,000 Pa*s. In some embodiments, the viscosity is no greater than 5000 or 2500 Pa*s at room temperature.

In some embodiments, the polymerizable dental compositions may include a wide variety of "other" ethylenically unsaturated monomers (with or without acid functionality), epoxy-functional (meth)acrylate resins, vinyl ethers, and the like.

In some embodiments, the polymerizable dental compositions may further include one or more ethylenically unsaturated compounds with acid functionality. For example, inclusion of such compounds may be useful for polymerizable dental compositions intended to exhibit self-adhesive properties, i.e., that do not require a separate step of etching with an acid to promote bonding of the dental composition to a dental structure. Surprisingly, particularly with respect- to self-adhesive compositions, it was discovered that the cyclic imide monomers of the present disclosure are more efficient as stress reducing agents than known addition-fragmentation agents. More specifically, it was discovered that the cyclic imide monomers of the present disclosure, in combination with acidic monomers, exhibit a significantly greater percentage of stress reduction per weight employed relative to known addition-fragmentation agents, exhibit strong self-adhesive properties, and maintain adequate levels of other desired properties.

In some embodiments, the acid functionality may include an oxyacid (i.e., an oxygen-containing acid) of carbon, sulfur, phosphorous, or boron. As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

In some embodiments, ethylenically unsaturated compounds with acid functionality include, for example, α,β-unsaturated acidic compounds such as glycerol phosphate mono(meth)acrylates, glycerol phosphate di(meth)acrylates, hydroxyethyl (meth)acrylate (e.g., HEMA) phosphates, bis ((meth)acryloxyethyl) phosphate, ((meth)acryloxypropyl) phosphate, bis((meth)acryloxypropyl) phosphate, bis((meth) acryloxy)propyloxy phosphate, (meth)acryloxyhexyl phosphate, bis((meth)acryloxyhexyl) phosphate, (meth)acryloxyoctyl phosphate, bis((meth)acryloxyoctyl) phosphate, (meth)acryloxydecyl phosphate, bis((meth)acryloxydecyl) phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly (meth)acrylated polyboric acid, and the like, may be used as components. Also monomers, oligomers, and polymers of unsaturated carbonic acids such as (meth)acrylic acids, aromatic (meth)acrylated acids (e.g., methacrylated trimellitic acids), and anhydrides thereof can be used.

In some embodiments, the polymerizable dental compositions can include an ethylenically unsaturated compound with acid functionality having at least one P—OH moiety. Such compositions are self-adhesive and are non-aqueous. For example, such compositions can include: a first compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a $C_1$-$C_4$ hydrocarbon group; a second compound including at least one (meth)acryloxy group and at least one —O—P(O) (OH)X group, wherein x=1 or 2, and wherein the at least one —O—P(O)(OH)X group and the at least one (meth)acryloxy group are linked together by a $C_5$-$C_{12}$ hydrocarbon group; an ethylenically unsaturated compound without acid functionality; an initiator system; and a filler.

In some embodiments, the polymerizable dental compositions may include solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water.

In some embodiments, the polymerizable dental compositions can contain additives such as indicators, dyes, pigments, inhibitors, accelerators, viscosity modifiers, wetting agents, buffering agents, radical and cationic stabilizers (e.g., BHT), and other similar ingredients that will be apparent to those skilled in the art. Medicaments or other therapeutic substances can be added to the polymerizable dental compositions. Examples include fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents (in addition to the antimicrobial lipid component), antifungal agents, agents for treating xerostomia, desensitizers, and the like, of the type often used in dental compositions. Combinations of any of the above additives may also be employed. The selection and amount of any one such additive can be selected by one of skill in the art to accomplish the desired result without undue experimentation.

In some embodiments, the concentration of a component in the polymerizable/hardenable dental composition described herein can be expressed with respect to the (i.e., unfilled) curable component (or polymerizable resin portion) of the dental composition. In some embodiments, where the composition further includes filler, the concentration of a component can also be expressed with respect to the total (i.e., filled) composition. When the composition is free of filler, the curable component (or polymerizable resin portion) is the same as the total composition.

In some embodiments, the unfilled polymerizable dental composition may include between 0.1 wt-% and 30 wt-%, between 0.1 wt-% and 10 wt-%, between 0.1 wt-% and 5 wt-%, or between 0.5 wt-% and 5 wt-% of an addition-fragmentation agent that includes any of the above-described cyclic imide monomers, based on the total weight of the unfilled polymerizable dental composition.

In embodiments that include an addition-fragmentation agent in addition to those that include a cyclic imide monomer, the unfilled polymerizable dental composition may include between 0.1 wt-% and 30 wt-%, between 0.1 wt-% and 10 wt-%, between 0.1 wt-% and 5 wt-%, or between 0.5 wt-% and 5 wt-% of a non-cyclic imide monomer including addition-fragmentation agent, based on the total weight of the unfilled polymerizable dental composition.

In some embodiments, the unfilled polymerizable dental composition may include between 10 wt-% and 95 wt-%, between 15 wt-% and 45 wt-%, or between 25 wt-% and 40% wt-% of at least one ethylenically unsaturated monomer or oligomer (other than addition-fragmentation agents), based on the total weight of the unfilled polymerizable dental composition.

In some embodiments, the unfilled polymerizable dental composition may include between 10 wt-% and 95 wt-%, between 10 wt-% and 40 wt-%, or between 15 wt-% and 30 wt-% of ethylenically unsaturated isocyanurate monomer(s), based on the total weight of the unfilled polymerizable dental composition.

In some embodiments, the unfilled polymerizable dental composition may include at least 1 wt-%, at least 3 wt-%, or at least 5 wt-% ethylenically unsaturated compounds with acid functionality, based on the total weight of the unfilled composition. In some embodiments, the unfilled polymerizable dental composition may include at most 80 wt-%, at most 70 wt-%, or at most 60 wt-% ethylenically unsaturated compounds with acid functionality, based on the total weight of the unfilled composition.

Materials with high polymerization stress upon curing generate strain in the tooth structure. One clinical consequence of such stress can be a decrease in the longevity of the restoration. The stress present in the composite passes through the adhesive interface to the tooth structure generating cuspal deflection and cracks in the surrounding dentin and enamel which can lead to postoperative sensitivity as described in R. R. Cara et al, Particulate Science and Technology 28; 191-206 (2010). In some embodiments, (e.g., filled) dental compositions (useful for restorations such as fillings and crowns) described herein typically exhibit a stress deflection of no greater than 2.0, or 1.8, or 1.6, or 1.4, or 1.2 or 1.0 or 0.8 or 0.6 microns.

In some embodiments, the inclusion of the addition-fragmentation agent(s) provides a significant reduction in stress even though the stress deflection is greater than 2.0 microns. For example, the inclusion of the addition-fragmentation agent(s) may reduce the stress from about 7 microns to about 6, or about 5, or about 4, or about 3 microns.

In some embodiments, the polymerizable dental compositions, in addition to the curable component, may include one or more fillers. Fillers may be selected from one or more of a wide variety of materials suitable for incorporation in compositions used for dental applications, such as fillers currently used in dental restorative compositions, and the like.

In some embodiments, the filler can be an inorganic material. It can also be a crosslinked organic material that is insoluble in the polymerizable resin, and is optionally filled with inorganic filler. The filler is generally non-toxic and suitable for use in the mouth. The filler can be radiopaque, radiolucent, or nonradiopaque. Fillers as used in dental applications are typically ceramic in nature.

Non-acid-reactive inorganic filler particles include quartz (i.e., silica), submicron silica, zirconia, submicron zirconia, and non-vitreous microparticles of the type described in U.S. Pat. No. 4,503,169 (Randklev).

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than 12 micrometers, typically no greater than 10 micrometers, and more typically no greater than 5 micrometers as measured using, for example, a sedimentation particle size analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, MN), FUJI II LC and FUJI IX (G-C Dental Industrial Corp., Tokyo, Japan) and CHEMFIL Superior (Dentsply International, York, PA). Mixtures of fillers can be used if desired.

Other suitable fillers are disclosed in U.S. Pat. No. 6,387,981 (Zhang et al.) and U.S. Pat. No. 6,572,693 (Wu et al.) as well as PCT International Publication Nos. WO 01/30305 (Zhang et al.), U.S. Pat. No. 6,730,156 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. Pat. No. 7,090,721 (Craig et al.), U.S. Pat. No. 7,090,722 (Budd et al.) and U.S. Pat. Nos. 7,156,911; and 7,649,029 (Kolb et al.).

Examples of suitable organic filler particles include filled or unfilled pulverized polycarbonates, polyepoxides, poly (meth)acrylates and the like. Commonly employed dental filler particles are quartz, submicron silica, and non-vitreous microparticles of the type described in U.S. Pat. No. 4,503,169 (Randklev).

Mixtures of these fillers can also be used, as well as combination fillers made from organic and inorganic materials.

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

Micron-size particles are very effective for improving post-cure wear properties. In contrast, nanoscopic fillers are commonly used as viscosity and thixotropy modifiers. Due to their small size, high surface area, and associated hydrogen bonding, these materials are known to assemble into aggregated networks.

In some embodiments, the polymerizable dental compositions may include nanoscopic particulate fillers (i.e., a filler that comprises nanoparticles) having an average primary particle size of less than about 0.100 micrometers (i.e., microns), or less than 0.075 microns. As used herein, the term "primary particle size" refers to the size of a non-associated single particle. The average primary particle size can be determined by cutting a thin sample of hardened dental composition and measuring the particle diameter of about 50-100 particles using a transmission electron micrograph at a magnification of 300,000 and calculating the average. The filler can have a unimodal or polymodal, (e.g., bimodal) particle size distribution. The nanoscopic particulate material typically has an average primary particle size of at least about 2 nanometers (nm), or at least about 7 nm. In some embodiments, the nanoscopic particulate material has an average primary particle size of no greater than about 50 nm, or no greater than about 20 nm in size. The average surface area of such a filler may be at least about 20 square meters per gram ($m^2/g$), at least about 50 $m^2/g$, or at least about 100 $m^2/g$.

In some embodiments, the polymerizable dental compositions include silica nanoparticles. Silica particles may be made from an aqueous colloidal dispersion of silica (i.e., a sol or aquasol). The colloidal silica is typically in the concentration of about 1 to 50 weight percent in the silica sol. Colloidal silica sols that can be used are available commercially having different colloid sizes, see Surface & Colloid Science, Vol. 6, ed. Matijevic, E., Wiley Interscience, 1973. Some silica sols for use making the fillers are supplied as a dispersion of amorphous silica in an aqueous medium and those which are low in sodium concentration and can be acidified by admixture with a suitable acid (e.g. Ludox colloidal silica made by E. I. Dupont de Nemours & Co.).

In some embodiments, the silica particles in the sol have an average particle diameter of about 5-100 nm, 10-50 nm, or 12-40 nm.

In some embodiments, the dental composition comprises zirconia nanoparticles.

Suitable nano-sized zirconia nanoparticles can be prepared using hydrothermal technology as described in U.S. Pat. No. 7,241,437 (Davidson et al.).

In some embodiments, lower refractive index (e.g., silica) nanoparticles are employed in combination with high refractive index (e.g., zirconia) nanoparticles in order to index match (refractive index within 0.02) the filler to the refractive index of the polymerizable resin.

In some embodiments, the nanoparticles are in the form of nanoclusters, i.e., a group of two or more particles associated by relatively weak intermolecular forces that cause the particles to clump together, even when dispersed in a hardenable resin, Nanoclusters can include a substantially amorphous cluster of non-heavy (e.g., silica) particles, and amorphous heavy metal oxide (i.e., having an atomic number greater than 28) particles such as zirconia. The particles of the nanocluster may have an average diameter of less than about 100 nm. Suitable nanocluster fillers are described in U.S. Pat. No. 6,730,156 (Windisch et al.); incorporated herein by reference in its entirety.

In some embodiments, the polymerizable dental compositions may include nanoparticles and/or nanoclusters surface treated with an organometallic coupling agent to enhance the bond between the filler and the resin. The organometallic coupling agent may be functionalized with reactive curing groups, such as acrylates, methacrylates, vinyl groups and the like.

Suitable copolymerizable organometallic compounds may have the general formulas: $CH_2=C(CH_3)_mSi(OR)_n$ or $CH_2=C(CH_3)_mC=OOASi(OR)_n$; wherein m is 0 or 1, R is an alkyl group having 1 to 4 carbon atoms, A is a divalent organic linking group, and n is from 1 to 3. Suitable coupling agents include gamma-methacryloxypropyltrimethoxysilane, gamma-mercaptopropyltriethoxysilane, gamma-aminopropyltrimethoxysilane, and the like.

In some embodiments, a combination of surface modifying agents can be useful, wherein at least one of the agents has a functional group co-polymerizable with a hardenable resin. Other surface modifying agents which do not generally react with hardenable resins can be included to enhance dispersibility or rheological properties. Examples of silanes of this type include, for example, aryl polyethers, alkyl, hydroxy alkyl, hydroxy aryl, or amino alkyl functional silanes.

The surface modification can be done either prior to mixing with the monomers or after mixing. It is typical to combine the organosilane surface treatment compounds with nanoparticles before incorporation into the resin. The required amount of surface modifier is dependent upon several factors such as particle size, particle type, modifier molecular wt, and modifier type. In general, approximately a monolayer of modifier may be attached to the surface of the particle.

In embodiments having fillers, the polymerizable dental compositions may include any of the above-described fillers (including any combinations thereof) in an amount between 1 wt-% and 95 wt-%, between 5 and 90 wt-%, between 30 and 90 wt-%, between 50 and 90 wt-%, or between 55 and 85 wt-%, based on the total weight filled polymerizable dental composition. In some embodiments useful as dental restoratives, the polymerizable dental compositions may include any of the above-described fillers (including any combinations thereof) in an amount between 70 wt-% and 90 wt-% or between 72 and 85 wt-%, based on the total weight filled polymerizable dental composition. In some embodiments useful as flowable adhesives, the polymerizable dental compositions may include any of the above-described fillers (including any combinations thereof) in an amount between 55 wt-% and 70 wt-% or between 58 and 65 wt-%, based on the total weight filled polymerizable dental composition.

In some embodiments, the polymerizable dental compositions can be used to treat an oral surface such as tooth, as known in the art. In some embodiments, the compositions can be hardened by curing after applying the dental composition. For example, when the curable dental composition is used as a restorative such as a dental filling, the method generally comprises applying the polymerizable dental composition to an oral surface (e.g., a cavity); and curing the composition. In some embodiments, a dental adhesive may be applied prior to application of the polymerizable dental restoration material described herein. Dental adhesives are also typically hardened by curing concurrently with curing the highly filled polymerizable dental restoration composition. The method of treating an oral surface may comprise providing a dental article and adhering the dental article to an oral (e.g., a tooth) surface.

In other embodiments, the polymerizable dental compositions can be hardened into dental articles prior to applying. For example, a dental article such as a crown may be pre-formed from the hardenable dental composition described herein. Dental composite articles (e.g., crowns) can be made from the polymerizable dental composition described herein by casting the composition in contact with a mold and curing the composition. Alternatively, dental composite article (e.g., crowns) can be made by first curing the composition forming a mill blank and then mechanically milling the composition into the desired article.

Another method of treating a tooth surface comprises providing a polymerizable dental composition as described herein wherein the composition is in the form of a (partially hardened) hardenable, self-supporting, malleable structure having a first semi-finished shape; placing the hardenable dental composition on a tooth surface in the mouth of a subject; customizing the shape of the hardenable dental composition; and hardening the hardenable dental composition. The customization can occur in the patient's mouth or on a model outside the patient mouth such as described in U.S. Pat. No. 7,674,850 (Karim et al.); incorporated herein by reference.

Objects and advantages are further illustrated by the following examples, but the particular materials and amounts thereof recited in these examples, as well as other conditions and details, should not be construed to unduly limit this invention. Unless otherwise indicated, all parts and percentages are on a weight basis.

EXAMPLES

Unless otherwise noted, all parts, percentages, ratios, etc. in the Examples and the rest of the specification are by weight. Unless otherwise indicated, all other reagents were obtained, or are available from fine chemical vendors such as Sigma-Aldrich Company, St. Louis, Missouri, or may be synthesized by known methods. Table 1 (below) lists materials used in the examples and their sources.

TABLE 1

Materials List

| DESIGNATION | DESCRIPTION | SOURCE |
|---|---|---|
| Cyclohexane | Cyclohexane | EMD Chemicals, Inc., Gibbstown, NJ, USA |
| Hexane | Hexane | EMD Chemicals, Inc. |
| Dichloromethane | Dichloromethane | EMD Chemicals, Inc. |
| Ethyl acetate | Ethyl acetate | EMD Chemicals, Inc. |

TABLE 1-continued

Materials List

| DESIGNATION | DESCRIPTION | SOURCE |
|---|---|---|
| Acetic anhydride | Acetic anhydride | EMD Chemicals, Inc. |
| Glycidyl methacrylate | Glycidyl methacrylate | Alfa Aesar, Haverhill, MA, USA |
| Dibutyltin dilaurate | Dibutyltin dilaurate | Alfa Aesar |
| IEM | 2-isocyanatoethyl methacrylate | TCI Chemicals, Tokyo, Japan |
| Methyl methacrylate oligomer mixture | | Prepared as described below |
| Potassium hydroxide | KOH | Sigma Aldrich, St. Louis, MO, USA |
| Methyl methacrylate dimer | | Prepared as described below. |
| Concentrated HCl | Hydrochloric acid | Sigma Aldrich |
| Diacid 1 | HO-C(O)-C(CH$_3$)$_2$-CH$_2$-C(=CH$_2$)-C(O)-OH (structure shown) | Prepared as described below. |
| Anhydride 2 | (cyclic anhydride structure shown) | Prepared as described below. |
| β-alanine | Beta-alanine | Sigma Aldrich |
| Ph$_3$P | Triphenyl phosphine, P(C$_6$H$_5$)$_3$ | Sigma Aldrich |
| Ph$_3$Sb | Triphenyl antimony, (C$_6$H$_5$)$_3$Sb | Sigma Aldrich |
| 6-amino caproic acid | H$_2$N(CH$_2$)$_5$CO$_2$H | Sigma Aldrich |
| 12-aminododecanoic acid | NH$_2$(CH$_2$)$_{11}$COOH | Sigma Aldrich |
| 3-amino-1-propanol | HO(CH$_2$)$_3$NH$_2$ | Sigma Aldrich |
| 5-amino-1-pentanol | HO(CH$_2$)$_5$NH$_2$ | Alpha Aesar |
| 3-amino-1,2-propanediol | NH$_2$CH$_2$CH(OH)CH$_2$OH | Sigma Aldrich |
| Silica sol | 41.33 wt. % 20 nanometer methoxy propanol, obtained under the trade nanosilica designation "NALCO 2329k" | Nalco Company, Naperville, IL, USA |
| 1-methoxy-2-propanol | CH$_3$OCH$_2$CH(CH$_3$)OH | Alpha Aesar |
| Prostab | Hydroxy TEMPO | Sigma Aldrich |
| 3-methacryloxy propyl trimethoxysilane | (MeO)$_3$SiCH$_2$CH$_2$OC(O)C(CH$_3$)CH$_2$ | Sigma Aldrich |
| Pentaerythritol triacrylate | (H$_2$C=CHCO$_2$CH$_2$)$_3$CCH$_2$OH | Sigma Aldrich |
| IRG651 | UV photoinitiator obtained under the trade designation "IRGACURE 651" | BASF, Ludwigshafen, Germany |
| 1,6-diaminohexane | H$_2$N(CH$_2$)$_6$NH$_2$ | Sigma Aldrich |
| 1,8-diaminooctane | NH$_2$(CH$_2$)$_8$NH$_2$ | Sigma Aldrich |
| 1,12-Diaminododecane | NH$_2$(CH$_2$)$_{12}$NH$_2$ | Sigma Aldrich |
| BHT | Butylated hydroxytoluene | Sigma Aldrich |

TABLE 2

List of Additional Materials for Dental Paste Composites

| DESIGNATION | DESCRIPTION | SOURCE |
|---|---|---|
| ERGP-IEM | The synthesis of ERGP-IEM is described in U.S. Pat. No. 8,710,113 (ER = ethoxylated resorcinol; GP = glycidyl phenyl ether (CAS# 122-60-1); IEM = 2-isocyanatoethyl methacrylate) | 3M Company internally prepared |
| BisGMA | Bisphenol A diglycidyl dimethacrylate (A.K.A. 2,2-bis[4-(2-hydroxy-3-methacryloyloxypropoxy)phenyl]propane) | Sigma Aldrich |
| HEMA | 2-hydroxyethyl methacrylate | Sigma Aldrich |
| UDMA | Urethane dimethacrylate (CAS# 11-0004-2577-4) | Esstech Inc, (Essington, PA, USA) |
| DDDMA | 1,12-dodecanediol dimethacrylate (CAS# 11-0024-2745-5) | Sartomer Co, Exton, PA |
| EDMAB | ethyl 4-(dimethylamino)benzoate (CAS# 11-0003-5273-9) | Sigma Aldrich |
| CPQ | Camphorquinone (CAS# 11-0042-2433-0 or 11-0003-5451-1 | Sigma Aldrich |
| BZT | Benzotriazole (CAS# 11-0018-0180-9) | Ciba, Inc., Tarrytown, N.Y |
| BHT | butylated hydroxytoluene (CAS# 11-0003-0076-1) | Sigma Aldrich |
| DPIHFP | diphenyliodoniumm hyxafluorophosphate (CAS# 11-0018-0679-0) | Alpha Aesar, Ward Hill, Mass |

TABLE 2-continued

List of Additional Materials for Dental Paste Composites

| DESIGNATION | DESCRIPTION | SOURCE |
| --- | --- | --- |
| MDP | 10-methacryloyloxydecyl phosphate; (2-Propenoic acid, 2-methyl-, reaction products with 1,10-decanediol and phosphorus oxide (P2O5)) (CAS# 1207736-18-2) | 3M Company prepared internally |
| Silica/Zirconia silane treated clusters | Silane-treated silica-zirconia nanocluster filler, prepared as described in U.S. Pat. No. 6,730,156. | 3M Company prepared |
| Silane treated nanozirconia filler | Silane-treated zirconia filler—described in U.S. Pat. No. 8,647,510 | 3M Company prepared |
| Silane treated 20 nm silica filler | silane-treated silica nanoparticle filler—described in U.S. Pat. No. 6,572,693 | 3M Company prepared |
| YbF3 | Ytterbium fluoride (100 nm) | Sukgyung AT Co. Ltd-Korea |
| Z250 | 3M ™ Filtek ™ Z250 Universal Restorative | 3M Company, St. Paul, MN, USA |
| AFM1 | Addition Fragmentation Monomer 1 (Preparation described below) | 3M Company prepared |

Test Methods:

Stress Test Method (Cusp Deflection): To measure stress development during the curing process, a slot was machined into a rectangular 8×10×15 mm aluminum block with a slot of 4×4×8 mm to contain the dental compositions being tested. A linear variable displacement transducer (Model GT 1000, used with an E309 analog amplifier, both from RDP Electronics, United Kingdom) was positioned as shown to measure the displacement of the cusp tip as the dental composition photocured at room temperature. Prior to testing, the slot in the aluminum block was sandblasted using Rocatec Plus Special Surface Coating Blasting Material (3M), treated with RelyX Ceramic Primer (3M), and finally treated with a dental adhesive, Scotchbond Universal (3M). The slot was fully packed with the EXAMPLE mixtures shown in the tables, which equaled approximately 100 mg of material. The material was irradiated for 1 minute with a Elipar S-10 dental curing light (3M) positioned almost in contact (<1 mm) with the material in the slot. Then, 9 minutes after the curing light was extinguished, the displacement of the cusp (cusp deflection) was measured in microns. A lower value of cusp deflection indicated less polymerization shrinkage stress (PSS) exerting on a surrounding substrate (tooth) during actual dental restoration procedure.

Depth of Cure Test (DOC) Method: The depth of cure was determined by filling a 10 millimeter stainless steel mold cavity with the composite, covering the top and bottom of the mold with sheets of polyester film, pressing the sheets to provide a leveled composition surface, placing the filled mold on a white background surface, irradiating the dental composition for 10 or 20 seconds, as indicate, using a dental curing light (3M Dental Products Curing Light Elipar S-10) positioned almost in contact (<1 mm) with the material in the slot, separating the polyester films from each side of the mold, gently removing (by scraping) materials from the bottom of the sample (i.e., the side that was not irradiated with the dental curing light), and measuring the thickness of the remaining material in the mold. The reported depths are the measured cured thickness in millimeters divided by 2.

Barcol Hardness Test Method: An uncured composite sample was cured in a 2.5-mm or 4-mm thick TEFLON mold sandwiched between a sheet of polyester (PET) film and a glass slide for 10 or 20 seconds, as indicated, and cured with an Elipar S-10, 3M dental curing light (3M Company). After irradiation, the PET film was removed and the hardness of the sample at both the top and the bottom of the mold was measured using a Barber-Coleman Impressor (a hand-held portable hardness tester; Model GYZJ 934-1; Barber-Coleman Company, Industrial Instruments Division, Lovas Park, Ind.) equipped with an indenter. Top and bottom Barcol Hardness values were measured immediately after light exposure.

Diametral Tensile Strength (DTS): DTS was measured per the following procedure. The uncured composite sample was injected into a glass tube that was about 30 mm long with a 4-mm inside diameter. It was filled about ½ full and capped with silicone rubber plugs. The tube was compressed axially at approximately 3 kg/cm$^2$ pressure for 5 minutes. While still under pressure, the sample was then light cured for 60 seconds by exposure to a dental curing light with a radiant exitance of greater than 1000 mW/cm$^2$. The tube was rotated as it cured to ensure equal exposure. A Buehler Iso Met 4000 (Illinois Tool Works, Lake Bluff, 111., USA) saw was then used to section disks about 2 mm thick from the tube. The resulting disks were stored in distilled water at 37° C. for about 24 hours prior to testing. Measurements were carried out using an appropriate materials test frame (eg. Instron 5966, Instron Corp., Canton, Mass.) with a 10 kilonewton load cell at a crosshead speed of 1 mm per minute. Diametral tensile strength was calculated as describe in Craig's Restorative Dental Materials, (Ronals L. Sakaguchi and John M. Powers. "Testing of Dental Materials and Biomechanics." Craig's Restorative Dental Materials, thirteenth ed., [0286] Elsevier, 2012, p. 86)

Adhesion Shear Bond Strength to Enamel or Dentin Test Method: Adhesive shear bond strength to enamel or dentin for Examples was evaluated by the following procedure.

Preparation of Teeth: Bovine incisal teeth, free of soft tissue, were embedded in circular acrylic disks. The embedded teeth were stored in water in a refrigerator prior to use. In preparation for adhesive testing, the embedded teeth were ground to expose a flat enamel or dentin surface using 120-grit sandpaper mounted on a lapidary wheel. Further grinding and polishing of the tooth surface was done using 320-grit sandpaper on the lapidary wheel. The teeth were continuously rinsed with water during the grinding process. The polished teeth were stored in deionized water and used for testing within 2 hours after polishing. The teeth were allowed to warm in a 36° C. oven to between room temperature (23° C.) and 36° C. before use.

Teeth Treatment: A 2.5-mm thick Teflon mold with a hole approximately 4.7 mm in diameter was clamped to the embedded tooth such that the hole in the mold exposed part of the adhesively prepared tooth surface (enamel or dentin). Example material was filled into the hole such that the hole was completely filled, but not overfilled, and light cured for 20 seconds to form a "button" that was adhesively attached to the tooth.

Adhesive Bond Strength Testing: The adhesive strength of a cured test example was evaluated by mounting the assembly (described above) in a holder clamped in the jaws of an INSTRON testing machine (Instron Corp. Canton, Mass.) with the polished tooth surface oriented parallel to the direction of pull. A loop of orthodontic wire (0.44-mm diameter) was placed around the Example button adjacent to the polished tooth surface. The ends of the orthodontic wire were clamped in the pulling jaw of the INSTRON apparatus and pulled at a crosshead speed of 2 mm/min, thereby placing the adhesive bond in shear stress. The force in kilograms (kg) at which the bond failed was recorded, and this number was converted to a force per unit area (units of MPa) using the known surface area of the button. Each reported value of adhesion to enamel or adhesion to dentin represents the average of 4 to 5 replicates.

Cyclic Imide Addition-Fragmentation Monomer Synthesis

General Procedures. All reactions were performed in round-bottomed flasks or glass jars/vials using unpurified commercial reagents.

Instrumentation. Proton nuclear magnetic resonance ($^1$H NMR) spectra and carbon nuclear magnetic resonance ($^3$C NMR) spectra were recorded on a 500 MHz spectrometer.

Distillation of Methyl Methacrylate Oligomer Mixture

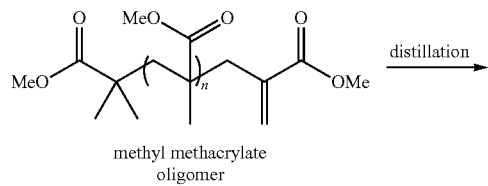

methyl methacrylate oligomer

A methyl methacrylate oligomer mixture was prepared according to the procedure described in Example 1 of U.S. Pat. No. 4,547,323 (Carlson, G. M.). The mixture was distilled as described in Moad, C. L.; Moad, G.; Rizzardo, E.; and Thang, S. H. Macromolecules, 1996, 29, 7717-7726, with details as follows:

A 1 liter (L) round-bottomed flask equipped with a magnetic stir bar was charged with 500 grams (g) of methyl methacrylate oligomer mixture. The flask was fitted with a Vigreux column, a condenser, a distribution adapter, and four collection flasks. With stirring, the distillation was placed under reduced pressure (0.25 mm Hg). The oligomer mixture was stirred under reduced pressure at room temperature until gas evolution (removal of methyl methacrylate monomer) had largely subsided. The distillation pot was then heated to reflux in an oil bath to distill the oligomer mixture at reduced pressure to provide the desired dimer.

Hydrolysis of Methyl Methacrylate Dimer

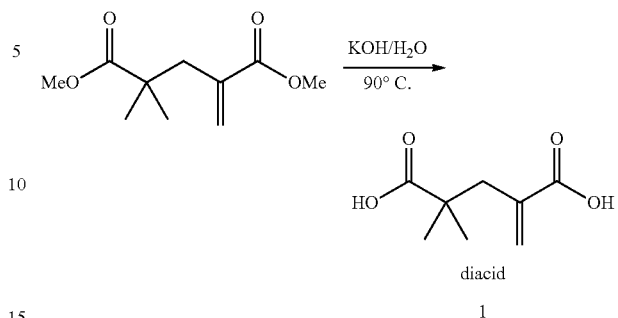

diacid
1

The dimer was hydrolyzed to diacid 1 as described in Hutson, L.; Krstina, J.; Moad, G.; Morrow, G. R.; Postma, A.; Rizzardo, E.; and Thang, S. H. Macromolecules, 2004, 37, 4441-4452, with details as follows:

Diacid 1. A 1 L, round-bottomed flask equipped with a magnetic stir bar was charged with deionized (DI) water (302 milliliters (mL)) and potassium hydroxide (90.46 g, 1612 millimole (mmol)). The mixture was stirred until homogeneous. Methyl methacrylate dimer (120.0 g, 599.3 mmol) was added. The reaction was equipped with a reflux condenser and was heated to 90° C. in an oil bath. After 17 hours, the reaction was removed from the oil bath and was allowed to cool to room temperature. The reaction solution was acidified to pH ~0 using concentrated HCl. A white precipitate formed upon acidification. The heterogeneous mixture was vacuum filtered and the white solid was washed quickly with DI water (twice with 50-100 mL). The white solid was then recrystallized from DI water (220 mL). The recrystallized solid was collected via vacuum filtration using a Buchner funnel. The collected solids were then quickly washed with DI water (twice with 50 mL). The solid was further dried under high vacuum to provide diacid 1 (86.67 g, 503.4 mmol, 84%) as a fine white solid.

Preparation of Cyclic Imide Monomers

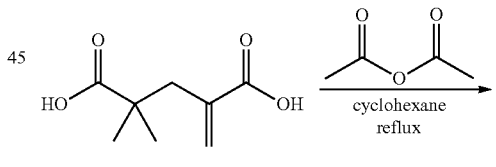

1

2

Anhydride 2. A 1 L round-bottomed flask equipped with a magnetic stir bar was charged with diacid 1 (50.00 g, 290.4 mmol), cyclohexane (500 mL), and acetic anhydride (73.30 mL, 79.16 g, 775.4 mmol). The reaction flask was equipped with a Dean-Stark trap and a reflux condenser. With, stirring, the reaction was heated to reflux in an oil bath. The solution was refluxed for 2 hours during which approximately 200 mL of colorless liquid was removed from the Dean-Stark trap. After 2 hours, the reaction was removed from the oil bath and was allowed to cool to room temperature. A white solid precipitated out of solution as it cooled. The precipitate was collected via vacuum filtration using a Buchner funnel and was quickly washed with cyclohexane (75 mL). The white solid was then recrystallized from cyclohexane (400 mL). The recrystallized solid was collected via vacuum filtration using a Buchner funnel and was washed with cyclohexane (2×75 mL). The solid was further dried under high vacuum to provide anhydride 2 (34.83 g, 225.9 mmol, 78%) as a white crystalline solid.

Methacrylate-functionalized addition-fragmentation cyclic imide monomers (CIMs) CIM-2, CIM-4, and CIM-6 were prepared (Table A) from the corresponding carboxylic acid-functionalized cyclic imides and glycidyl methacrylate (Reaction Scheme 6). Acid functional imides CIM-1, CIM-3, and CIM-5 (Table A) were prepared through condensation of the corresponding amino acid and a cyclic anhydride prepared from a methacrylate dimer (Reaction Scheme 5).

Methacrylate-functionalized addition-fragmentation cyclic imide monomers (CIMs) CIM-8 and CIM-10 and acid functional imides CIM-7, CIM-9, and CIM-11 were also prepared similarly to Reaction Scheme 6 utilizing hydroxyl-functional amines, 3-amino-1-propanol, 5-amino-1-pentanol, 3-amino-1,2-propanediol. For some compounds the hydroxyl group was reacted with 2-isocyanatoethyl methacrylate.

The structures of the synthesized addition-fragmentation cyclic imide monomers are depicted in Table A.

CIM-1. An approximately 40 mL amber glass bottle equipped with a magnetic stir bar was charged with anhydride 2 (15.00 g, 97.30 mmol) and β-alanine (8.668 g, 97.30 mmol). The two solid reagents were mixed well using a wooden applicator. The reaction was sealed with a Teflon-lined plastic cap. With stirring, the mixture was heated to 125° C. in an oil bath. After 4 hours, the reaction was removed from the oil bath, the cap was removed, and the reaction mixture was allowed to cool to room temperature open to the atmosphere. The crude product mixture was purified by filtering twice through a plug of silica gel (~4 cm wide by 10 cm tall) using a 50:50 mixture of hexane and ethyl acetate as eluent to provide CIM-1 (13.835 g, 61.42 mmol, 63%) as a white solid. $^1$H NMR analysis was consistent with the desired product.

CIM-2. An approximately 8 mL amber glass vial equipped with a magnetic stir bar was charged with CIM-1 (2.00 g, 8.879 mmol) and glycidyl methacrylate (1.262 g, 8.878 mmol), and triphenyl antimony (0.0188 g, 0.0532 mmol). The reaction was sealed with a Teflon-lined plastic cap. With stirring, the mixture was heated to 100° C. in an oil bath. After 18 hours, triphenyl phosphine (0.0046 g, 0.0178 mmol) was added. The reaction was kept stirring at 100° C. After an additional 9 hours, the reaction was sampled and $^1$H NMR analysis was consistent with the desired product as a mixture of isomers. The reaction was cooled to room temperature to provide CIM-2 (3.224 g, 8.775 mmol, 99%) as a clear, colorless viscous oil.

CIM-3. An approximately 80 mL amber glass bottle equipped with a magnetic stir bar was charged with anhydride 2 (15.00 g, 97.30 mmol) and 6-amino caproic acid (12.764 g, 97.30 mmol). The two solid reagents were mixed well using a wooden applicator. The reaction was sealed with a Teflon-lined plastic cap. With stirring, the mixture was heated to 125° C. in an oil bath. After 4 hours, the reaction was removed from the oil bath, the cap was removed, and the reaction mixture was allowed to cool to room temperature open to the atmosphere. The crude product mixture was purified by filtering twice through a plug of silica gel (~4 cm wide by 10 cm tall) using a 50:50 mixture of hexane and ethyl acetate as eluent for the first filtration and 75:25 hexane and ethyl acetate as eluent for the second filtration to provide CIM-3 (14.606 g, 54.64 mmol, 56%) as a white solid. $^1$H NMR analysis was consistent with the desired product.

CIM-4. An approximately 20 mL glass vial equipped with a magnetic stir bar was charged with CIM-3 (2.22 g, 8.305 mmol) and glycidyl methacrylate (1.180 g, 8.301 mmol), and triphenyl antimony (0.0176 g, 0.0498 mmol). The reaction was sealed with a Teflon-lined plastic cap. With stirring, the mixture was heated to 100° C. in an oil bath. After 18 hours, triphenyl phosphine (0.0044 g, 0.0166 mmol) was added. The reaction was kept stirring at 100° C. After an additional 9 hours, the reaction was cooled to room temperature and sampled. $^1$H NMR analysis revealed a small amount of unreacted epoxide. The reaction was reheated to 100° C. After 6 hours, the reaction was cooled to room temperature and sampled. $^1$H NMR analysis revealed a small amount of unreacted epoxide. The reaction was reheated to 100° C. After 23 hours, the reaction was cooled to room temperature and sampled. $^1$H NMR analysis was consistent with the desired product as a mixture of isomers. The reaction provided CIM-4 (3.359 g, 8.203 mmol, 99%) as a pale yellow viscous oil.

CIM-5. An approximately 80 mL glass bottle equipped with a magnetic stir bar was charged with anhydride 2 (10.00 g, 64.87 mmol) and 12-aminododecanoic acid (13.968 g, 64.87 mmol). The two solid reagents were mixed well using a wooden applicator. The reaction vessel was then capped with a screw-on vacuum adapter left open to the atmosphere. With stirring, the mixture was heated to 125° C. in an oil bath. After 50 minutes, the reaction was placed under vacuum (~0.3 mm Hg). After 4 hours, the reaction was removed from the oil bath, the cap was removed, and the reaction mixture was allowed to cool to room temperature open to the atmosphere. The crude product mixture was taken up in dichloromethane (100 mL) and then vacuum filtered via Buchner funnel to remove insoluble material. The filtered dichloromethane solution was concentrated in vacuo. The residue was redissolved in a 60:40 mixture of hexane and ethyl acetate and purified by filtering through a plug of silica gel (~4 cm wide by 10 cm tall) using a 60:40 mixture of hexane:ethyl acetate as eluent. The filtered solution was then concentrated in vacuo. The silica gel filtration was repeated twice more to provide CIM-5 (11.910 g, 33.89 mmol, 52%) as a clear, colorless, viscous oil. $^1$H NMR analysis was consistent with the desired product.

CIM-6. An approximately 20 mL glass vial equipped with a magnetic stir bar was charged with CIM-5 (5.000 g, 14.23 mmol) and glycidyl methacrylate (2.02 g, 14.21 mmol), and triphenyl antimony (0.0301 g, 0.0852 mmol). The reaction was sealed with a Teflon-lined plastic cap. With stirring, the mixture was heated to 100° C. in an oil bath. After 24 hours, triphenyl phosphine (0.0075 g, 0.0286 mmol) was added. The reaction was kept stirring at 100° C. After an additional 18 hours, the reaction was sampled and $^1$H NMR analysis was consistent with the desired product as a mixture of isomers. The reaction was cooled to room temperature to provide CIM-6 (7.012 g, 14.20 mmol, 100%) as a viscous yellow oil.

CIM-7. An approximately 240 mL amber glass bottle with Teflon-wrapped threads and equipped with a magnetic stir bar was charged with anhydride 2 (25.00 g, 162.2 mmol) and then placed in a room-temperature water bath. Next, 3-amino-1-propanol (12.3 mL, 12.18 g, 162.2 mmol) was added over 5 minutes. The bottle was then equipped with a lid adapted to apply vacuum. The bottle was placed in a 125° C. oil bath and stirred. After 30 minutes at 125° C., the reaction was placed under vacuum. After an additional 4 hours, the reaction was backfilled with nitrogen and allowed to cool to room temperature to provide a clear yellow viscous liquid. The reaction was opened to the atmosphere and dissolved in a 90:10 mixture of dichloromethane and ethyl acetate. The crude product mixture was purified by filtering twice through a plug of silica gel (~7.5 cm wide by 15 cm tall) using a 90:10 mixture of dichloromethane and ethyl acetate as eluent. The eluent was concentrated in vacuo to a colorless oil. The crude product mixture was further purified by filtering twice more through a plug of silica gel (~7.5 cm wide by 15 cm tall) using a 90:10 mixture of dichloromethane and ethyl acetate as eluent for the first filtration and a gradient from 95:5 to 90:10 mixture of dichloromethane and ethyl acetate as eluent to provide CIM-7 (11.13 g, 52.68 mmol, 32%) as a colorless oil. $^1$H NMR analysis was consistent with the desired product.

CIM-8. An approximately 30 mL glass vial equipped with a magnetic stir bar was charged with CIM-7 (3.00 g, 14.2 mmol) and 2-isocyanatoethyl methacrylate (2.01 mL, 2.20 g, 14.2 mmol), and one drop of dibutyltin dilaurate from a pipette tip. The reaction was sealed with a Teflon-lined plastic cap. With stirring, the mixture was heated to 50° C. in an oil bath. After 48 hours, the reaction was sampled and $^1$H NMR analysis was consistent with the desired product. The reaction was cooled to room temperature to provide CIM-8 (4.946 g, 14.11 mmol, 99%) as a clear, colorless viscous oil.

CIM-9. An approximately 240 mL amber glass bottle with Teflon-wrapped threads and equipped with a magnetic stir bar was charged with anhydride 2 (25.00 g, 162.2 mmol) and then placed in a room-temperature water bath. Next, 5-amino-1-pentanol (17.5 mL, 16.7 g, 162.2 mmol) was added over 10 minutes. The bottle was placed in a 125° C. oil bath with stirring and open to the atmosphere. After 30 minutes, the bottle was equipped with a lid adapted to apply vacuum and the reaction was placed under vacuum. After an additional 3.5 hours, the reaction allowed to cool to room temperature and opened to the atmosphere to provide a clear yellow sticky material. The reaction was opened to the atmosphere and dissolved in a 90:10 mixture of dichloromethane and ethyl acetate. The crude product mixture was purified by filtering four times through a plug of silica gel (~2.5 cm wide by 12.5 cm tall) using a 90:10 mixture of dichloromethane and ethyl acetate as eluent. After the final silica gel plug filtration, the eluent was concentrated in vacuo to a colorless viscous oil. This oil was further dried by bubbling air through the material using an 18 gauge needle to provide CIM-9 (11.91 g, 49.78 mmol, 31%) as a clear, colorless viscous liquid. $^1$H NMR analysis was consistent with the desired product.

CIM-10. An approximately 30 mL glass vial equipped with a magnetic stir bar was charged with CIM-9 (5.00 g, 20.9 mmol) and 2-isocyanatoethyl methacrylate (2.95 mL, 3.24 g, 20.9 mmol), and one drop of dibutyltin dilaurate from a pipette tip. The reaction was sealed with a Teflon-lined plastic cap. With stirring, the mixture was heated to 50° C. in an oil bath. After 168 hours, the reaction was sampled and $^1$H NMR analysis was consistent with the desired product. The reaction was cooled to room temperature to provide CIM-10 (8.199 g, 20.78 mmol, 99%) as a clear, colorless viscous liquid.

CIM-11. An approximately 240 mL glass bottle with Teflon-wrapped threads and equipped with a magnetic stir bar was charged with anhydride 2 (25.00 g, 162.2 mmol) and (+/−) 3-amino-1,2-propanediol (14.78 g, 162.2 mmol). The bottle was then equipped with a lid adapted to apply vacuum. The bottle was placed in a 125° C. oil bath and stirred. After 15 minutes at 125° C., the reaction was placed under active vacuum. The active vacuum was shut off and the reaction was left under static vacuum for 5 minutes and then placed briefly back under active vacuum. This was sequence was repeated twice more and then the reaction was left under static vacuum with stirring at 125° C. for 4 hours. The reaction was then backfilled with nitrogen and allowed to cool to room temperature to provide a yellow/orange glass solid. The crude reaction product was dissolved in dichloromethane with the aid of sonication for 30 minutes. The crude product mixture was then by filtered through a plug of silica gel (~12.5 cm wide by 7.5 cm tall) using a 97:3 mixture of dichloromethane and methanol as eluent. The eluent was concentrated in vacuo to a colorless viscous liquid. The crude product mixture was once more filtered through a plug of silica gel (~12.5 cm wide by 7.5 cm tall) using a 95:05 mixture of dichloromethane and methanol as eluent to provide CIM-11 (11.87 g, mmol, 32%) as a colorless oil. $^1$H NMR analysis was consistent with the desired product.

AFM1 Synthesis:

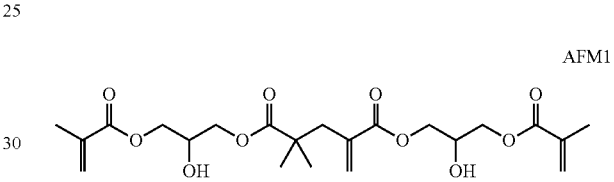

AFM1. An approximately 250 mL amber bottle equipped with a magnetic stir bar was charged with glycidyl methacrylate (23.0 mL, 24.8 g, 174 mmol) and triphenyl antimony (0.369 g, 1.04 mmol). The reaction was covered with a plastic cap with two 16-gauge needles pierced through the cap to allow air into the reaction. With stirring, the mixture was heated to 100° C. in an oil bath. Diacid 1 (15.0 g, 87.1 mmol) was added to the reaction in small portions over a period of 1.5 hours. After 21 hours, triphenyl phosphine (0.091 g, 0.35 mmol) was added. The reaction was kept stirring at 100° C. After an additional 6.5 hours the reaction was sampled, and 1H NMR analysis was consistent with the desired product as a mixture of isomers and indicated consumption of glycidyl methacrylate. The reaction was cooled to room temperature to provide AFM1 as a clear, very pale-yellow viscous material.

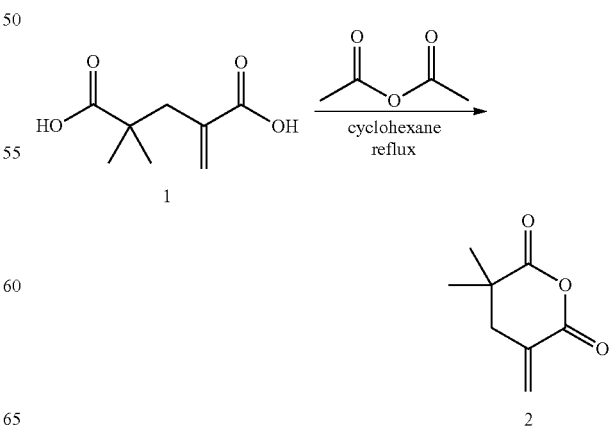

Anhydride 2. A 1 L round-bottomed flask equipped with a magnetic stir bar was charged with diacid 1 (50.00 g, 290.4 mmol), cyclohexane (500 mL), and acetic anhydride (73.30 mL, 79.16 g, 775.4 mmol). The reaction flask was equipped with a Dean-Stark trap and a reflux condenser. With, stirring, the reaction was heated to reflux in an oil bath. The solution was refluxed for 2 hours during which approximately 200 mL of colorless liquid was removed from the Dean-Stark trap. After 2 hours, the reaction was removed from the oil bath and was allowed to cool to room temperature. A white solid precipitated out of solution as it cooled. The precipitate was collected via vacuum filtration using a Buchner funnel and was quickly washed with cyclohexane (75 mL). The white solid was then recrystallized from cyclohexane (400 mL). The recrystallized solid was collected via vacuum filtration using a Buchner funnel and was washed with cyclohexane (2×75 mL). The solid was dried under reduced pressure to provide anhydride 2 (34.83 g, 225.9 mmol, 78%) as a white crystalline solid.

Bis Cyclic Imide Addition-Fragmentation Monomer Synthesis

Preparation of BCIM Monomers

Bis-cyclic imide monomers (BCIMs) BCIM-1, BCIM-2, and BCIM-3 that vary in chain length between the cyclic imide ends were prepared (Table A). The bis-imide monomers were prepared by cyclizing diacid 1 to anhydride 2 using acetic anhydride. Cyclic anhydride 2 was then condensed with the appropriate diamine to provide the bis-cyclic imide monomers (Reaction Scheme 7). The structures of the synthesized addition-fragmentation bis-cyclic imide monomers are depicted in Table A.

BCIM-1. An approximately 40 mL glass bottle equipped with a magnetic stir bar was charged with anhydride 2 (34.52 g, 223.92 mmol) and 1,6-diaminohexane (13.02 g, 111.96 mmol). The two solid reagents were mixed well using a wooden applicator. The reaction vessel was then capped with a screw-on vacuum adapter and placed under a nitrogen atmosphere. With stirring, the mixture was heated to 125° C. in an oil bath. After 20 minutes, the reaction was placed under vacuum (~0.3 mm Hg). After an additional 3 hours, the reaction was removed from the oil bath, the cap was removed, and the reaction mixture was allowed to cool to room temperature open to the atmosphere. The crude product mixture was taken up in dichloromethane (75 mL) and was filtered through a plug of silica gel (~4 cm wide by 10 cm tall) using an 80:20 mixture of hexane:ethyl acetate as eluent. The filtered solution was concentrated in vacuo. The silica gel filtration was repeated 5 more times. The product was then dried under high vacuum to provide BCIM-1 (8.3594 g, 21.52 mmol, 19.2%) as a white solid. $^1$H NMR analysis was consistent with the desired product.

BCIM-2. An approximately 40 mL glass bottle equipped with a magnetic stir bar was charged with anhydride 2 (10.00 g, 64.87 mmol) and 1,8-diaminooctane (4.679 g, 32.43 mmol). The two solid reagents were mixed well using a wooden applicator. The reaction vessel was then capped with a screw-on vacuum adapter. The flask was connected to a high vacuum line, but was left at atmospheric pressure. With stirring, the mixture was heated to 125° C. in an oil bath. After 35 minutes, the reaction was placed under vacuum (~0.3 mm Hg). After an additional 4 hours, the reaction was removed from the oil bath, the cap was removed, and the reaction mixture was allowed to cool to room temperature open to the atmosphere. The crude product mixture was taken up in dichloromethane (75 mL) and then vacuum filtered via Buchner funnel to remove insoluble material. The filtered dichloromethane solution was concentrated in vacuo. The residue was redissolved in dichloromethane and purified by filtering through a plug of silica gel (~4 cm wide by 10 cm tall) using dichloromethane as eluent. The filtered solution was then concentrated in vacuo. The silica gel filtration was repeated twice more. The product was then dried under high vacuum and further dried by bubbling air through the clear, colorless viscous liquid. The product solidified upon standing to provide BCIM-2 (2.6390 g, 6.335 mmol, 19.5%) as a white solid. $^1$H NMR analysis was consistent with the desired product.

BCIM-3. An approximately 40 mL glass bottle equipped with a magnetic stir bar was charged with anhydride 2 (10.00 g, 64.87 mmol) and 1,12-diaminododecane (6.4987 g, 32.44 mmol). The two solid reagents were mixed well using a wooden applicator. The reaction vessel was then capped with a screw-on vacuum adapter and placed under a nitrogen atmosphere. With stirring, the mixture was heated to 125° C. in an oil bath. After 50 minutes, the reaction was placed under vacuum (~0.3 mm Hg). After an additional 5 hours, the reaction was removed from the oil bath, the cap was removed, and the reaction mixture was allowed to cool to room temperature open to the atmosphere. The crude product mixture was taken up in dichloromethane (75 mL) and then vacuum filtered via Buchner funnel to remove insoluble material. The filtered dichloromethane solution was concentrated in vacuo. The residue was redissolved in an 80:20 mixture of hexane and ethyl acetate and purified by filtering through a plug of silica gel (~4 cm wide by 10 cm tall) using an 80:20 mixture of hexane:ethyl acetate as eluent. The filtered solution was concentrated in vacuo. The residue was redissolved in dichloromethane and purified by filtering through a plug of silica gel (~4 cm wide by 10 cm tall) using dichloromethane as eluent. The filtered solution was then concentrated in vacuo. The silica gel filtration was repeated once more using dichloromethane as eluent. The product was then dried under high vacuum and further dried by bubbling air through the clear, colorless viscous liquid. BCIM-3 (3.6170 g, 7.652 mmol, 23.6%) was obtained as a clear, colorless viscous liquid. $^1$H NMR analysis was consistent with the desired product.

Preparation of Hydroxy Bis-Cyclic Imide-1 (HBCIM-1)—Reaction Scheme 8

An amber glass bottle equipped with a magnetic stir bar is to be charged with 3,3-dimethyl-5-methylene-tetrahydropyran-2,6-dione (anhydride 2) and 1,3-diamino-2-propanol (0.5 equivalent of the anhydride 2). The two charged components will be mixed well using a wooden applicator. The bottle is then sealed with a Teflon-lined plastic cap. With stirring, the mixture is heated to 125° C. in an oil bath. After 4 hours, the reaction will be removed from the oil bath, the cap removed, and the reaction mixture will be allowed to cool to room temperature open to the atmosphere. The crude product mixture will then be purified by filtering twice through a plug of silica gel (approximately 4 centimeters wide by 10 centimeters tall) using a 50:50 mixture of hexane and ethyl acetate as eluent to provide the desired hydroxy bis-cyclic imide product, HBCIM-1.

Preparation of Methacrylated Hydroxy Bis-Cyclic Imide-1 (MA-BCIM-1)—Reaction Scheme 9

A glass jar is to be charged with HBCIM-1 and a 1 equivalent IEM. The components will be hand mixed using a wooden applicator. BHT (400 parts per million with respect to the total jar contents) and dibutyltin dilaurate catalyst (DBTDL, 0.5 wt %) will then be added to the jar followed by hand mixing. The jar will be left at room temperature for 30 minutes with hand mixing every 10 minutes. The jar will then be placed in an oven at 60° C. for 1 hour with hand mixing the components every 10-15 minutes to give the desired product MA-BCIM-1.

General Dental Examples Formulation Preparation:

Resin Samples were created by combining all components and heating (at 50° C.) until solids were completely dissolved (~90 min). Subsequent dental paste Examples using the stock resins were prepared by adding the ingredients into a 40 gram DAC cup followed by mixing in a speed mixer (Model DAC 150 FVZ SpeedMixer, manufactured by FlackTek, Inc., Landrum, S.C.) for 30-second intervals at 2500 rpm until the material was combined as indicated by a smooth homogenous composition. Examples that contain only AFM1 and no amount of CIM or BCIM are comparative examples

TABLE 3

Preparation of Resin Sample 1 and Resin Sample 2

| | Resin Sample 1 | | Resin Sample 2 | |
|---|---|---|---|---|
| Ingredients | amount (grams) | amount (%) | amount (grams) | amount (%) |
| ERGP-IEM | 24.09 | 69.4 | 103.99 | 69.4 |
| UDMA | 6.57 | 18.9 | 28.37 | 18.9 |
| DDDMA | 3.09 | 8.9 | 13.1 | 8.9 |
| EDMAB | 0.385 | 1.1 | 1.787 | 1.1 |
| CPQ | 0.098 | 0.3 | 0.417 | 0.3 |
| BZT | 0.175 | 0.5 | 0.759 | 0.5 |
| BHT | 0.175 | 0.5 | 0.074 | 0.5 |
| DPIHFP | 0.105 | 0.3 | 0.447 | 0.3 |
| total | 34.688 | 100.0 | 149.01 | 100.0 |

TABLE 4

Examples EX.1-EX.3 and Comparative Example 1 (CEx.1)

| Ingredients | EX.1 CIM7 (1.5) amount (%) | EX.2 CIM2 (1.5) amount (%) | EX.3 BCIM1 (1.5) amount (%) | CEx.1 AFM1 (1.5) amount (%) | Control 1 amount (%) |
|---|---|---|---|---|---|
| Resin Sample 1 (from Table 3) | 23.50 | 23.50 | 23.50 | 23.50 | 23.59 |
| Silica/Zirconia silane treated clusters | 65.86 | 65.86 | 65.86 | 65.86 | 66.09 |
| Silane treated nanozirconia filler | 1.60 | 1.60 | 1.60 | 1.60 | 1.61 |
| Silane treated 20 nm silica filler | 2.97 | 2.97 | 2.97 | 2.97 | 2.98 |
| YbF3 (100 nm) | 5.71 | 5.71 | 5.71 | 5.71 | 5.73 |
| CIM7, CIM2, BCIM1, or AFM additive | 0.36 | 0.36 | 0.36 | 0.36 | 0.0% |

TABLE 5

Resin Sample 2 + Cyclic Imides used in subsequent Examples

| Sample | Stock Resin Sample 2 (from Table 3) g/% | AFM1 | CIM2 | CIM7 | BCIM1 |
|---|---|---|---|---|---|
| Resin Sample 2 | 10.0 g 100% | 0 g 0% | — | — | — |
| Resin 2A AFM (1.5) | 10.0 g 98.52% | 0.15 g 1.48% | — | — | — |
| Resin 2B AFM (0.75) | 10.0 g 99.24% | 0.077 g 0.76% | — | — | — |
| Resin 2C AFM (0.75) CIM2 (0.75) | 10.0 g 98.51% | 0.077 g 0.76% | 0.075 g 0.74% | — | — |
| Resin 2D AFM (0.75) CIM7 (0.75) | 10.0 g 98.51% | 0.077 g 0.76% | — | 0.074 g 0.73% | — |
| Resin 2E AFM (0.75) BCIM1 (0.75) | 10.0 g 98.50% | 0.077 g 0.76% | — | — | 0.075 g 0.74% |
| Resin 2F CIM2 (0.75) | 9.925 g 99.25% | — | 0.075 g 0.75% | — | — |
| Resin 2G CIM7 (0.75) | 9.925 g 99.25% | — | — | 0.075 g 0.75% | — |
| Resin 2H BCIM1 (0.75) | 9.925 g 99.25% | — | — | — | 0.075 g 0.75% |

TABLE 6

Examples EX.4-EX.6 and Comparative Examples CEx.2, CEx.3

| Ingredients | Control 2 amount (%) | CEx.2 AFM (1.5) amount (%) | CEx.3 AFM (0.75) CIM2 (0.75) amount (%) | EX.4 AFM (0.75) CIM7 (0.75) amount (%) | EX.5 AFM (0.75) CIM7 (0.75) amount (%) | EX.6 AFM (0.75) BCIM1 (0.75) amount (%) |
|---|---|---|---|---|---|---|
| Resin Sample 2+ (from table 5) | Resin 2 23.92 | Resin 2A 23.88 | Resin 2B 24.02 | Resin 2C 24.10 | Resin 2D 24.01 | Resin 2E 24.00 |
| Silica/Zirconia silane treated clusters | 65.78 | 65.83 | 65.71 | 65.64 | 65.72 | 65.73 |
| Silane treated nanozirconia filler | 1.60 | 1.60 | 1.60 | 1.60 | 1.60 | 1.60 |
| Silane treated 20 nm silica filler | 2.97 | 2.97 | 2.97 | 2.97 | 2.97 | 2.96 |
| YbF3 (100 nm) | 5.73 | 5.71 | 5.70 | 5.70 | 5.70 | 5.70 |
| Total | 100.0% | 100.0% | 100.0% | 100.0% | 100.0% | 100.0% |

TABLE 7

Examples EX.7-EX.9

| | EXAMPLE | | |
|---|---|---|---|
| Ingredients | EX.7 CIM2 (0.75) amount (%) | EX.8 CIM7 (0.75) amount (%) | EX.9 BCIM1 (0.75) amount (%) |
| Resin Sample 2+ (from table 5) | Resin 2F 24.00 | Resin 2G 24.00 | Resin 2H 24.00 |
| Silica/Zirconia silane treated clusters | 65.73 | 65.73 | 65.73 |
| Silane treated nanozirconia filler | 1.60 | 1.60 | 1.60 |
| Silane treated 20 nm silica filler | 2.96 | 2.96 | 2.96 |
| YbF3 (100 nm) | 5.70 | 5.70 | 5.70 |
| Total | 100.0% | 100.0% | 100.0% |

TABLE 8

Stress Test and Depth of Cure Results: Examples EX.1-EX.9

| Example | Addition-fragmentation agent (wt %) | Stress Test (Cusp Deflection) avg (µm) | DOC 10 seconds avg (mm) | DOC 20 seconds avg (mm) |
|---|---|---|---|---|
| Control 2 | none | 9.82 | 3.77 | 5.21 |
| CEx.2 | AFM (1.5) | 8.01 | 3.83 | 5.21 |
| CEx.3 | AFM (0.75) | 8.39 | 4.23 | 5.10 |
| EX.2 | CIM2 (1.5) | 6.56 | 3.55 | 5.02 |
| EX.4 | AFM (0.75) CIM2 (0.75) | 6.95 | 3.98 | 5.08 |
| EX.7 | CIM2 (0.75) | 8.00 | n.m. | 5.06 |
| EX.1 | CIM7 (1.5) | 2.62 | 3.43 | 4.87 |
| EX.5 | AFM (0.75) CIM7 (0.75) | 4.72 | 4.24 | 4.78 |
| EX.8 | CIM7 (0.75) | 8.15 | n.m. | 5.00 |
| EX.3 | BCIM1 (1.5) | 4.51 | 3.08 | 4.76 |
| EX.6 | AFM (0.75) BCIM1 (0.75) | 4.13 | 3.89 | 4.71 |
| EX.9 | BCIM1 (0.75) | 5.12 | n.m. | 4.33 | n.m. = not measured

TABLE 9

Barcole Hardness Test Results: Examples EX.2-EX.9

| Example | Addition-fragmentation agent (wt %) | Barcole Hardness top (10 s) avg | Barcole Hardness bottom (10 s) avg | Barcole Hardness top (20 s) avg | Barcole Hardness bottom (20 s) avg |
|---|---|---|---|---|---|
| Control 2 | none | 76.40 | 76.80 | 65.20 | 75.80 |
| CEx.2 | AFM (1.5) | 75.80 | 76.70 | 72.00 | 76.00 |
| CEx.3 | AFM (0.75) | 64.00 | 73.80 | 72.60 | 72.80 |
| EX.2 | CIM2 (1.5) | 68.80 | 68.20 | n.m. | n.m. |
| EX.4 | AFM (0.75) CIM2 (0.75) | 69.00 | 70.40 | 72.60 | 75.40 |
| EX.7 | CIM2 (0.75) | 72.6 | 74.6 | n.m. | n.m. |
| EX.5 | AFM (0.75) CIM7 (0.75) | 56.80 | 65.00 | 60.80 | 69.20 |
| EX.8 | CIM 7 (0.75) | 73 | 74.8 | n.m. | n.m. |
| EX.3 | BCIM1 (1.5) | 49.60 | 51.00 | n.m. | n.m. |
| EX.6 | AFM (0.75) BCIM1 (0.75) | 57.80 | 65.80 | 66.40 | 67.00 |
| EX.9 | BCIM1 (0.75) | 62.8 | 65.2 | n.m. | n.m. | n.m. = not measured

TABLE 10

Diametral Tensile Strength (DTS) Test Results: Examples EX.1-EX.9

| Example | Addition-fragmentation agent (wt %) | DTS avg (MPa) |
|---|---|---|
| Control 2 | none | 79.90 |
| CEx.2 | AFM (1.5) | 79.29 |
| CEx.3 | AFM (0.75) | 76.41 |
| EX.2 | CIM2 (1.5) | 76.46 |
| EX.4 | AFM (0.75) CIM2 (0.75) | 70.52 |
| EX.7 | CIM2 (0.75) | 77.66 |
| EX.5 | CIM7 (1.5) | 63.10 |
| EX.8 | AFM (0.75) CIM7 (0.75) | 72.95 |
| EX.3 | CIM7 (0.75) | 72.53 |
| EX.6 | BCIM (1.5) | 69.57 |
| EX.9 | AFM (0.75) BCIM (0.75) | 72.41 |
| Control 2 | BCIM (0.75) | 74.16 |

TABLE 11

Preparation of Resin Sample 3 with Addition-fragmentation agents

| Name | Percentage (%) | Resin Sample 3 + AFM1 grams | Resin Sample 3 + CIM1 grams | Resin Sample 3 + CIM2 grams | Resin Sample 3 + BCIM1 grams |
|---|---|---|---|---|---|
| MDP | 23.58% | 2.36 | 2.36 | 2.36 | 2.36 |
| BisGMA | 40.51% | 4.05 | 4.05 | 4.05 | 4.05 |
| UDMA | 9.43% | 0.94 | 0.94 | 0.94 | 0.94 |
| HEMA | 18.87% | 1.89 | 1.89 | 1.89 | 1.89 |
| BHT | 0.27% | 0.03 | 0.03 | 0.03 | 0.03 |
| CPQ | 0.38% | 0.04 | 0.04 | 0.04 | 0.04 |
| EDMAB | 1.08% | 0.11 | 0.11 | 0.11 | 0.11 |
| DPIHFP | 0.49% | 0.05 | 0.05 | 0.05 | 0.05 |
| AFM1, CIM1, CIM2, or BCIM1 | 5.4% | 0.54 | 0.54 | 0.54 | 0.54 |

TABLE 12

Examples EX.10-EX.12 and Comparative Example CEx.4

| EXAMPLE Ingredients | CEx.4 AFM1 (5.4) amount (%) | EX.10 CIM1 (5.4) amount (%) | EX.11 CIM2 (5.4) amount (%) | EX.12 BCIM1 (5.4) amount (%) |
|---|---|---|---|---|
| Resin Sample 3 with Addition-fragmentation agent (from table 11) | 37.1% | 37.1% | 37.1% | 37.1% |
| Z250 | 57.9% | 57.9% | 57.9% | 57.9% |
| YbF3 (100 nm) | 5.0% | 5.0% | 5.0% | 5.0% |
| Total | 100.0% | 100.0% | 100.0% | 100.0% |

TABLE 13

DTS, Stress Test, and Depth of Cure Results: Examples EX.10-EX.12

| Example | Addition-fragmentation agent (wt. %) | DTS avg (MPa) | Stress Test (Cusp Deflection) avg (μm) | DOC 10 seconds avg (mm) |
|---|---|---|---|---|
| EX.10 | CIM1 (5.4) | 28.64 | 0.52 | 0.95 |
| EX.11 | CIM2 (5.4) | 27.36 | 0.50 | 1.08 |
| EX.12 | BCIM1 (5.4) | 40.81 | 0.50 | 1.07 |
| CEx.4 | AFM1 (5.4) | 74.86 | 6.17 | not measured |

TABLE 14

Preparation of Resin Sample 4 with various amounts of Addition-fragmentation agents

| Name | Resin Sample 4 + AFM1 (5.4) (%) | Resin Sample 4 + CIM1 (2.8) (%) | Resin Sample 4 + CIM2 (4.4) (%) | Resin Sample 4 + BCIM1 (1.9) (%) |
|---|---|---|---|---|
| MDP | 23.58% | 24.25% | 23.85% | 21.03% |
| BisGMA | 40.51% | 41.68% | 41.08% | 50.00% |
| UDMA | 9.43% | 9.62% | 9.62% | 8.45% |
| HEMA | 18.87% | 19.44% | 19.04% | 16.72% |
| BHT | 0.27% | 0.20% | 0.20% | 0.17% |
| CPQ | 0.38% | 0.40% | 0.40% | 0.34% |
| EDMAB | 1.08% | 1.20% | 1.00% | 1.03% |
| DPIHFP | 0.49% | 0.40% | 0.40% | 0.34% |
| AFM1, CIM1, CIM2, or BCIM1 | 5.39% | 2.81% | 4.41% | 1.90% |
| Total | 100.0% | 100.0% | 100.0% | 100.0% |

TABLE 15

Examples EX.13-EX.15 and Comparative Example CEx.5

| EXAMPLE Ingredients | CEx.5 AFM1 (5.4) amount (%) | EX.13 CIM1 (2.8) amount (%) | EX.14 CIM2 (4.4) amount (%) | EX.15 BCIM1 (1.9) amount (%) |
|---|---|---|---|---|
| Resin Sample 4 with Addition-fragmentation agent (from table 14) | 37.1% | 37.1% | 37.1% | 37.1% |
| Z250 | 57.9% | 57.9% | 57.9% | 57.9% |
| YbF3 (100 nm) | 5.0% | 5.0% | 5.0% | 5.0% |
| Total | 100.0% | 100.0% | 100.0% | 100.0% |

TABLE 16

DTS, Stress Test, DOC, and Barcol Hardness Results: Examples EX.13-EX.15

| Example | Addition-fragmentation agent (wt. %) | DTS avg (MPa) | Stress Test (Cusp Deflection) avg (μm) | DOC 10 seconds avg (mm) | Barcole Hardness top (20 s) avg |
|---|---|---|---|---|---|
| EX.13 | CIM1 (2.8) | 71.26 | 0.39 | 2.36 | 27.67 |
| EX.14 | CIM2 (4.4) | 72.23 | 0.65 | 2.40 | 27.00 |
| EX.15 | BCIM1 (1.9) | 65.06 | 1.28 | 2.32 | 32.67 |
| CEx.5 | AFM1 (5.4) | 70.58 | 4.11 | 2.44 | 65.50 |

TABLE 17

Preparation of Resin Sample 5 with various amounts of BCIM1

| Name | Resin Sample 5 for Control 3 (%) | Resin Sample 5 + BCIM1 (0.5) (%) | Resin Sample 5 + BCIM1 (1.0) (%) | Resin Sample 5 + BCIM1 (1.5) (%) |
|---|---|---|---|---|
| MDP | 24.92% | 24.80% | 24.67% | 24.59% |
| BisGMA | 42.82% | 42.69% | 42.39% | 42.20% |
| UDMA | 9.97% | 9.89% | 9.87% | 9.80% |
| HEMA | 19.95% | 19.79% | 19.75% | 19.60% |
| BHT | 0.29% | 0.28% | 0.28% | 0.28% |
| CPQ | 0.40% | 0.40% | 0.40% | 0.39% |
| EDMAB | 1.14% | 1.13% | 1.13% | 1.12% |
| DPIHFP | 0.52% | 0.51% | 0.51% | 0.51% |
| BCIM1 | 0.00% | 0.50% | 1.00% | 1.50% |
| Total | 100.0% | 100.0% | 100.0% | 100.0% |

TABLE 18

Preparation of Resin Sample 5 with various amounts of CIM2

| Name | Resin Sample 5 + AFM1 (5.4) (%) | Resin Sample 5 + CIM2 (0.5) (%) | Resin Sample 5 + CIM2 (1.0) (%) | Resin Sample 5 + CIM2 (1.5) (%) |
|---|---|---|---|---|
| MDP | 23.58% | 24.85% | 24.67% | 24.58% |
| BisGMA | 40.51% | 42.64% | 42.39% | 42.21% |
| UDMA | 9.43% | 9.89% | 9.87% | 9.80% |
| HEMA | 18.87% | 19.79% | 19.75% | 19.60% |
| BHT | 0.27% | 0.28% | 0.28% | 0.28% |
| CPQ | 0.38% | 0.40% | 0.40% | 0.39% |
| EDMAB | 1.08% | 1.13% | 1.13% | 1.12% |
| DPIHFP | 0.49% | 0.51% | 0.51% | 0.51% |
| CIM2 | 5.39% | 0.50% | 1.00% | 1.50% |
| Total | 100.0% | 100.0% | 100.0% | 100.0% |

TABLE 19

Examples EX.16-EX.21 and Comparative Example CEx.6

| Ingredients | Control 3 (No AFM) amount (%) | CEx.6 AFM1 (5.4) amount (%) | EX.16 BCIM1 (0.5) amount (%) | EX.17 BCIM1 (1.0) amount (%) | EX.18 BCIM1 (1.5) amount (%) | EX.19 CIM2 (0.5) amount (%) | EX.20 CIM2 (1.0) amount (%) | EX.21 CIM2 (1.5) amount (%) |
|---|---|---|---|---|---|---|---|---|
| Resin Sample 5 with Addition-fragmentation | 37.1% | 37.1% | 37.1% | 37.1% | 37.1% | 37.1% | 37.1% | 37.1% |

TABLE 19-continued

Examples EX.16-EX.21 and Comparative Example CEx.6

| Ingredients | Control 3 (No AFM) amount (%) | CEx.6 AFM1 (5.4) amount (%) | EX.16 BCIM1 (0.5) amount (%) | EX.17 BCIM1 (1.0) amount (%) | EX.18 BCIM1 (1.5) amount (%) | EX.19 CIM2 (0.5) amount (%) | EX.20 CIM2 (1.0) amount (%) | EX.21 CIM2 (1.5) amount (%) |
|---|---|---|---|---|---|---|---|---|
| agent (from tables 17 & 18) | | | | | | | | |
| Z250 | 57.9% | 57.9% | 57.9% | 57.9% | 57.9% | 57.9% | 57.9% | 57.9% |
| YbF3 (100 nm) | 5.0% | 5.0% | 5.0% | 5.0% | 5.0% | 5.0% | 5.0% | 5.0% |
| Total | 100.0% | 100.0% | 100.0% | 100.0% | 100.0% | 100.0% | 100.0% | 100.0% |

TABLE 20

DTS, Stress, DOC, Barcol Hardness, Adhesion Results: Examples EX.16-EX.21

| Example | Addition-frag. agent (wt. %) | DTS avg (MPa) | Stress Test (Cusp Deflect.) avg (μm) | DOC 10 seconds avg (mm) | Barcole Hardness top (20 s) avg | Barcole Hardness Bottom (20 s) avg | Enamel Adhesion Mean Shear Bond Strength MPa | Dentin Adhesion Mean Shear Bond Strength MPa |
|---|---|---|---|---|---|---|---|---|
| Control 3 | none | 72.89 | 4.58 | 2.31 | 63.5 | 64.7 | 6.35 | 4.96 |
| CEx.6 | AFM1 (5.4) | 78.32 | 5.88 | 2.43 | 72.2 | 68.5 | 8.35 | 7.45 |
| EX.16 | BCIM1 (0.5) | 79.44 | 5.19 | 2.29 | 62.3 | 53.5 | 4.79 | 4.16 |
| EX.17 | BCIM1 (1.0) | 71.50 | 5.30 | 2.32 | 65.0 | 62.3 | 5.10 | 5.17 |
| EX.18 | BCIM1 (1.5) | 61.19 | 5.79 | 2.33 | 68.0 | 65.2 | 5.55 | 6.30 |
| EX.19 | CIM2 (0.5) | 70.77 | 4.53 | 2.27 | 57.0 | 52.3 | 4.18 | 3.47 |
| EX.20 | CIM2 (1.0) | 79.20 | 4.80 | 2.36 | 57.5 | 54.7 | 6.01 | 5.37 |
| EX.21 | CIM2 (1.5) | 68.96 | 5.37 | 2.39 | 65.3 | 64.5 | 6.64 | 7.68 |

All cited references, patents, and patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:

1. A dental composition comprising:
   at least one monomer comprising at least two ethylenically unsaturated groups; and
   an addition-fragmentation agent comprising at least one cyclic imide monomer comprising an α, β-unsaturated carbonyl, wherein the cyclic imide monomer comprises an imide group and the α, β-unsaturated carbonyl in a heterocyclic ring wherein the ring comprises at least 6 covalently bonded atoms, and wherein the cyclic imide monomer further comprises a γ-quaternary carbon atom.

2. The dental composition of claim 1, wherein the cyclic imide monomer has the structure:

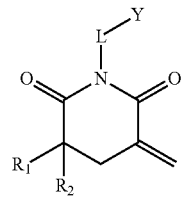

wherein L is a covalent bond or an organic linking group;
Y alkyl, aryl, hydroxyl, carboxylic acid, or an ethylenically unsaturated polymerizable group; and
$R_1$ and $R_2$ are independently alkyl groups.

3. The dental composition of claim 2, wherein $R_1$ and $R_2$ are substituents such that the cyclic imide monomer ring-opens during polymerization.

4. The dental composition of claim 2, wherein $R_1$ and $R^2$ are independently C1 to C18 alkyl groups.

5. The dental composition of claim 1, wherein L is (hetero)alkylene or (hetero)arylene.

6. The dental composition of claim 1, wherein Y is carboxylic acidic group or a (meth)acrylate group.

7. The dental composition of claim 1, wherein L comprises at least one hydroxyl group.

8. The dental composition of claim 1, wherein the cyclic imide monomer comprises at least two cyclic imide groups.

9. The dental composition of claim 1, wherein the cyclic imide monomer has the structure:

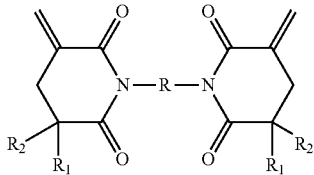

wherein R is an organic linking group; and
R₁ and R₂ are independently alkyl groups.

10. The dental composition of claim 9, wherein R₁ and R₂ are substituents such that the cyclic imide monomer ring-opens during polymerization.

11. The dental composition of claim 9, wherein R is (hetero)alkylene or (hetero)arylene, optionally comprising at least one pendent ethylenically unsaturated polymerizable group.

12. The dental composition of claim 1, further comprising a second addition-fragmentation agent comprising at least one ethylenically unsaturated terminal group and a backbone unit comprising an α, β-unsaturated carbonyl.

13. The dental composition of claim 12, wherein the second addition-fragmentation agent has the formula:

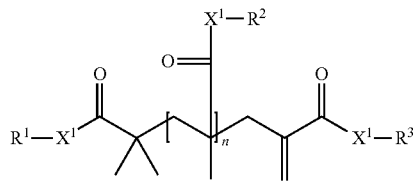

wherein
R¹, R² and R³ are each independently $Z_m$-Q-, a (hetero)alkyl group or a (hetero)aryl group with the proviso that at least one of R¹, R² and R³ is $Z_m$-Q-;
Q is a linking group have a valence of m+1;
Z is an ethylenically unsaturated polymerizable group;
m is 1 to 6;
each X¹ is independently —O— or —NR⁴—, where R⁴ is H or $C_1$-$C_4$ alkyl; and
n is 0 or 1.

14. The dental composition of claim 1 wherein the dental composition comprises at least one (meth)acrylate monomer selected from ethoxylated bisphenol A dimethacrylate (BisEMA6), 2-hydroxyethyl methacrylate (HEMA), bisphenol A diglycidyl dimethacrylate (bisGMA), urethane dimethacrylate (UDMA), triethlyene glycol dimethacrylate (TEGDMA), glycerol dimethacrylate (GDMA), ethylenegylcol dimethacrylate, neopentylglycol dimethacrylate (NPGDMA), polyethyleneglycol dimethacrylate (PEGDMMA), and mixtures thereof.

15. The dental composition of claim 1, wherein the dental composition comprises at least one monomer having an acid functional group, wherein the acid functional group comprises a carboxylic acid, phosphoric acid, phosphonic acid, or sulfonic acid functional group.

16. The dental composition of claim 1, wherein the unfilled dental composition comprises between 0.1 wt-% and 30 wt-% of the cyclic imide monomer, based on the total weight of the unfilled dental composition.

17. A method of treating a tooth surface, the method comprising
providing the dental composition of claim 1;
placing the dental composition on a tooth surface in the mouth of a subject; and
hardening the dental composition.

18. A composition comprising:
at least one monomer comprising at least two ethylenically unsaturated groups; and
an addition-fragmentation agent comprising at least one cyclic imide monomer comprising an α, β-unsaturated carbonyl.

* * * * *